(12) United States Patent
Lauto et al.

(10) Patent No.: US 9,029,349 B2
(45) Date of Patent: May 12, 2015

(54) BIOADHESIVE FOR TISSUE REPAIR

(75) Inventors: Antonio Lauto, Leichhardt (AU); Laura Poole-Warren, Coogee (AU); Leslie John Ray Foster, Narara (AU)

(73) Assignee: Antonio Lauto, Coogee NSW (AU)

( * ) Notice: Subject to any disclaimer, the term of this patent is extended or adjusted under 35 U.S.C. 154(b) by 1665 days.

(21) Appl. No.: 11/661,087

(22) PCT Filed: Aug. 26, 2005

(86) PCT No.: PCT/AU2005/001297
§ 371 (c)(1),
(2), (4) Date: Oct. 31, 2007

(87) PCT Pub. No.: WO2006/021054
PCT Pub. Date: Mar. 2, 2006

(65) Prior Publication Data
US 2008/0132467 A1    Jun. 5, 2008

(30) Foreign Application Priority Data

Aug. 27, 2004 (AU) ................................. 2004904914
Jan. 5, 2005 (AU) ................................. 2005900035

(51) Int. Cl.
*A61L 24/08* (2006.01)
*A61P 43/00* (2006.01)
*A61B 17/03* (2006.01)
*A61L 24/00* (2006.01)

(52) U.S. Cl.
CPC .............. *A61L 24/001* (2013.01); *A61L 24/08* (2013.01)

(58) Field of Classification Search
None
See application file for complete search history.

(56) References Cited

U.S. PATENT DOCUMENTS

| 5,747,475 A | 5/1998 | Nordquist et al. |
| 5,837,747 A | 11/1998 | Soon-Shiong |
| 5,948,427 A | 9/1999 | Yamamoto |
| 6,239,190 B1 | 5/2001 | Wilkinson |
| 6,800,671 B1 * | 10/2004 | Montgomery et al. ....... 523/105 |
| 6,869,938 B1 * | 3/2005 | Schwartz et al. ............... 514/57 |

FOREIGN PATENT DOCUMENTS

| EP | 1 106 189 A2 | 6/2001 |
| WO | WO 92/02238 | 2/1992 |
| WO | WO 96/38093 | 12/1996 |
| WO | WO 01/58430 A1 | 8/2001 |

OTHER PUBLICATIONS

Berger, J. et al., European Journal of Pharmaceutics and Biopharmaceutics, "Structure and interactions in covalently and ionically crosslinked chitosan hydrogels for biomedical applications", (Jan. 2004), vol. 57, pp. 19-34.*
Draget, K. I., Polymer Gels and Networks, "Associating phenomena in highly acetylated chitosan gels", (1996), vol. 4, pp. 143-151.*
Atmospheric Science Data Center, "What Wavelength Goes With a Color", also available at http://eosweb.larc.nasa.gov/EDDOCS/Wavelengths_for_Colors.html; last viewed Sep. 23, 2010.*
Ono, Katsuaki et al., "Photocrosslinkable chitosan as a biological adhesive", Journal of Biomedical Materials Research, 2000, pp. 289-295, vol. 49, John Wiley & Sons, Inc.
Supplementary European Search Report issued in corresponding European Application No. EP 05 77 6240, with a date of completion on Sep. 21, 2010, two (2) pages.

* cited by examiner

*Primary Examiner* — Layla Bland
*Assistant Examiner* — Bahar Craigo
(74) *Attorney, Agent, or Firm* — Nath, Goldberg & Meyer; Tanya E. Harkins

(57) ABSTRACT

The invention provides a bioadhesive composition comprising a polysaccharide and an energy converter, wherein the energy converter is activated by non-UV light. The composition may be prepared by dissolving the polysaccharide and the energy converter in an aqueous acidic solution. The composition, in the form of a film or a gel, may be used for repairing a discontinuity in an area of tissue or for joining tissue.

12 Claims, 20 Drawing Sheets

BIOADHESIVE FOR TISSUE REPAIR

TECHNICAL FIELD

The present invention relates to biomaterials with adhesive properties and use thereof in tissue repair. In particular, the present invention relates to compositions comprising polysaccharides and a light converter, for use in tissue repair. More particularly, the present invention relates to bioadhesive gels and films for use in tissue repair.

BACKGROUND OF THE INVENTION

Wound closure by suturing or stapling is the standard surgical technique currently used in hospitals. There are considerable disadvantages related to this technique, including foreign tissue reaction to suture materials, such as nylon threads, which are not absorbed by the body. Suturing techniques are also very difficult to perform during certain surgical procedures, for example, endoscopy procedures where the limitation in free movements and vision imposed by the minimally invasive nature of such procedures are a serious impairment for doctors. Another limitation is that sutures/staples are not usually used to carry drugs and deliver them to the wound site to improve the healing process. They may also result in poor sealing.

Photo-activated bioadhesives are biomaterials capable of adhering to tissue following exposure of the biomaterial to light and represent an alternative to sutures. Bioadhesives have significant advantages with respect to sutures because they are minimally invasive for the host tissue and they may be absorbed by the body over a period of time. In comparison with sutures and staples, they may also decrease the amount of time required during a surgical procedure.

U.S. Pat. No. 6,323,037 discloses a fluid protein solder composition comprising an active compound (such as a protein or a peptide), a solvent and an energy converter, which is insoluble in physiological fluids. A method of welding a tissue is also disclosed which comprises contacting a tissue with the solder composition and exciting the composition so that the tissue becomes welded.

U.S. Pat. No. 6,211,335 discloses a fluid protein solder composition comprising a water soluble protein, water and optionally a dye. The protein-based solder can be preformed as a preformed strip or can be applied as drops across the edges of tissue to be joined. Upon exposure to an energy source the solder melts and welds the tissue together.

U.S. Pat. No. 6,583,117 discloses a method of welding tissue by applying a biodegradable biological solder across the edges of tissue and exposing the solder to an energy source under conditions which cause the solder to bond to tissue surfaces adjacent the edges to provide a weld and thereby join the tissue together. The solder compositions are based on protein (e.g., albumin) which are denatured upon exposure to thermal energy (at temperatures >50° C.), or light energy from an energy source.

AU 768533 discloses a solder composition for use in welding biological tissue comprising a denatured proteinaceous substance. The solder composition is adapted to melt during use in order to weld between tissue surfaces together.

A disadvantage of protein-based solders is that they have a relatively weak tensile strength, with the consequence that a relatively large amount of solder has to be dispensed onto repair sites to ensure proper bonding and prevent tissue dehiscence. Furthermore, protein compositions which are soluble in water must be coagulated at 65-70° C. by laser light to become insoluble and achieve satisfactory weld strength. Another drawback of tissue welding is that the thermal denaturation process, which is essential to form the weld, may result in tissue damage or cell death. A further disadvantage of blood-based products, such as albumin glues or solders, is the there is an associated disease transmission risk.

Laser-activated solders for tissue repair are traditionally based on three proteins: albumin, fibrinogen and collagen. The first two are blood-derived and therefore have an intrinsic, although limited, risk of viral infection for the host organism. Albumin solders are the most investigated and is promising candidates for specific procedures in urology, vascular surgery and microsurgery due to their bonding characteristics. Nevertheless, the use of albumin solders, especially in the solid form, is limited by their water solubility, lack of flexibility and brittleness before being irradiated by lasers. These disadvantages, along with the potential thermal damage to tissue caused by the laser, may compromise the safe and reliable application of solders in surgical procedures. It is not surprising therefore, that clinicians and surgeons are reluctant to routinely employ albumin solders for tissue repair and wound closure.

There is a need for a biocompatible adhesive material of sufficient tensile strength and biocompatible properties which can be used with a reduced risk of causing thermal damage to tissue.

SUMMARY OF THE INVENTION

According to a first aspect of the invention there is provided a composition comprising a polysaccharide and an energy converter wherein the energy converter is activatable by non-UV light.

According to a second aspect of the invention there is provided a composition comprising a polysaccharide and an energy converter, wherein the energy converter is activatable by non-UV light and is not activatable by UV light.

The composition may be a bioadhesive composition. The composition may be in the form of a film or a gel.

According to a third aspect of the invention there is provided a bioadhesive film comprising a polysaccharide and an energy converter, wherein the energy converter is activatable by non-UV light. It may be activatable by visible light and/or may be activatable by IR (infrared) light.

The energy converter may be a light converter. The energy converter may not absorb UV light, and may absorb non-UV light. The light converter, or energy converter, may absorb, or be capable of absorbing, visible and/or infrared light. The energy converter may be an energy absorber, and may be a light absorber. It may be a dye or a pigment.

The polysaccharide may be a polymeric polysaccharide. In one embodiment, the polysaccharide is positively charged. In another embodiment the polysaccharide is negatively charged. In one embodiment, a positively charged polysaccharide may electrostatically associate with anionic groups on a compound or tissue. In an alternative embodiment, a negatively charged polysaccharide may electrostatically associate with cationic groups on a compound or tissue. In one embodiment, a positively charged polysaccharide may associate with anionic groups on collagen. In another embodiment a negatively charged polysaccharide may associate with cationic groups on collagen.

The polysaccharide may be selected from aminopolysaccharides such as chitosan, heparin sulfate, chondroitin sulfate, beta-glucans, carrageenan, xantham gum, guar gum, locust bean gum, pectin, galactomannan, and acidic polysaccharides such as hyaluronic acid and alginate.

In some embodiments of the invention the polysaccharide is chitosan or chitin. The degree of deacetylation of chitosan may be in a range from about 0% to about 95%, or from about 0% to about 90%, or from about 0 to 70, 0 to 50, 0 to 30, 0 to 10, 20 to 90, 40 to 90, 60 to 90, 10 to 80, 30 to 60 or 40 to 60% for example, about 0%, about 10%, about 15%, about 20%, about 25%, about 30%, about 35%, about 40%, about 45%, about 50%, about 55%, about 60%, about 65%, about 70%, about 75%, about 80%, about 85%, about 90%, or greater than about 90%, where the percentages are weight % or mol %. Chitin may be regarded as chitosan having a degree of deacetylation of 0%.

In some embodiments of the invention, the polysaccharide may be unmodified, i.e. the polysaccharide may not be covalently linked to a photoreactive group. In other embodiments of the invention, the polysaccharide may be modified, i.e. the polysaccharide may be covalently linked to a photoreactive group, such as for example, a vinyl group or a naphthalimide group. The photoreactive group may be UV-activatable group, for example a UV-activatable crosslinker. The photoreactive group may be different to the energy converter.

The light converter, or energy converter, may be activatable by light of wavelength ≥400 nm. The wavelength of light used to activate the light converter, or energy converter, may be in the visible, near-IR, mid-IR, or far-IR range. For example, the energy converter may be a light converter capable of absorbing light of wavelength in a range from about 400 nm to about 10.6 micron, or about 400 nm to 5 microns, 400 nm to 1 micron, 400 to 800 nm, 400 to 700 nm, 400 to 600 nm, 500 to 600 nm, 500 to 700 nm, 600 to 700 nm, 700 nm to 1 micron, 1 to 10.6 micron, 5 to 10.6 micron, 500 nm to 5 micron, 500 nm to 1 micron, 1 to 2 microns, 2 to 5 microns, 2 to 5 microns, to 10.6 microns, 5 to 10 microns or 1 to 5 microns. For example, the wavelength may be in a range from about 450 nm to about 850 nm, about 500 nm to about 850 nm, about 550 nm to about 850 nm, about 600 nm to about 840 nm, about 650 nm to about 830 nm, about 700 nm to about 820 nm, about 750 to about 820 nm, or about 800 to about 820 nm.

In various embodiments of the invention, the light converter, or energy converter, may be capable of being activated by light of wavelength of about 750-850 nm, for example, about 780-820 nm, 790-815 nm, 800-810 nm. In various embodiments, the light converter, or energy converter, is capable of being activated by light of wavelength about 795 nm, about 796 nm, about 797 nm, about 798 nm, about 799 nm, about 800 nm, about 801 nm, about 802 nm, about 803 nm, about is 804 nm, about 805 nm, about 806 nm, about 807 nm, about 808 nm, about 809 nm, about 810 nm, about 811 nm, about 812 nm, about 813 nm, about 814 nm, about 815 nm, about 816 nm, about 817 nm, about 818 nm, about 819 nm or about 820 nm.

The light source may be a laser. Examples of suitable light sources include diode lasers, e.g. GaAlAs diode lasers (e.g. emitting at 808 nm), Nd:YAG lasers, Argon lasers and $CO_2$ lasers, Holmium:Yag lasers, Erbium:Yag lasers and $CO_2$ lasers. The laser may be coupled with an articulated arm, optical fibre, e.g. a multimode optical fibre, single mode or multimode crystal fibre, single mode or multimode polymer crystal fibre.

In one embodiment of the invention the light source may be a Nd:YAG laser and the wavelength of light used to activate the energy converter may be about 1-1.1 micron, e.g, 1.06 micron. In another embodiment, the light source may be a Ho:YAG laser and the wavelength of light used to activate the light converter, or energy converter, is about 2-2.5 micron, e.g. 2.1 micron.

In a further embodiment, the light source is an Er:YAG laser and the wavelength of light used to activate the light converter, or energy converter, is about 2.5-3 micron, e.g., 2.94 micron. In another embodiment, the light source is a $CO_2$ laser and the wavelength of light used to activate the light converter, or energy converter, is about 10.5-11 micron, e.g. 10.6 micron.

In one embodiment, the light converter, or energy converter, is not capable of absorbing UV light.

In one embodiment, one or more light converters and/or energy converters may be present. Respective light converters and/or energy converters may be the same or different.

In various embodiments of the invention, the light converter, or energy converter, may be water, $D_2O$ or carboxylated camphorquinone. In other embodiments the light converter or energy converter is a dye. The dye may be an infrared dye, including near-IR. In various embodiments the dye may be capable of absorbing light of wavelength 750-850 nm. In other embodiments, the light converter or energy converter may be a dye selected from a genipin dye, squid ink, melanin, and indocyanine green. In one embodiment, the dye is indocyanine green. The light converter or energy converter may not be a UV light photoinitiator.

The energy converter may be added separately to the composition. In an alternative embodiment, the energy converter (e.g, a light converter) may be attached (e.g, ionically or covalently attached) to the polysaccharide. The energy converter may act by absorbing non-UV light and converting photons into heat. Alternatively, the energy converter may act as a photo-initiator and convert light into chemical energy. For example, photons may be absorbed by a photoinitiator that creates free radicals which may crosslink the polymers. A photo-initiator (e.g, carboxylated camphorquinone) may promote cross-linking of a cross-linking agent (e.g, 4-vinylbenzoic acid) which has been added to the polysaccharide, or may promote cross-linking of the polysaccharide.

In one embodiment, a light converter or energy converter (e.g. a genipin dye) may also function as a cross-linker.

The polysaccharide may cross-link with tissue with which it is in contact (including, for example, cross-linking with collagen in tissue). The light converter or energy converter may cross-link the polysaccharide.

The concentration of the light converter or energy converter in the composition or film may be about 0.01 to about 5 wt %, e.g. about 0.01 to about 4 wt %, about 0.01 to about 3 wt %, about 0.01 to about 2 wt %, about 0.01 to about 1 wt %, about 0.015 to about 1 wt %, about 0.02 to about 0.75 wt %, about 0.025 to about 0.7 wt %, about 0.03 to about 0.65 wt %, about 0.035 to about 0.6 wt %, about 0.04 to about 0.05 wt %, and may be about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5 or 5 wt %.

Films according to the invention may have a thickness of about 5 μm to about 5 mm, for example, from about 5 μm to about 4.75 mm, about 10 μm to about 4.5 mm, about 15 μm to about 4.5 mm, about 20 μm to about 4.25 mm, about 30 μm to about 4 mm, about 40 μm to about 3.75 mm, about 50 μm to about 3.5 mm, about 60 μm to about 3.25 mm, about 70 μm to about 3 mm, about 80 to about 2.75 mm, about 90 μm to about 2.5 mm, about 100 μm to about 2.25 mm, about 110 μm to about 2 mm, about 120 μm to about 1.75 mm, about 130 μm to about 1.5 mm, about 140 μm to about 1.25 mm, about 150 μm to about 1 mm, about 175 μm to about 750 μm, about 200 μm to about 500 μm, about 300 μm to about 400 μm or about 15 μm to about 30 μm, and may be about 5, 10, 15, 20, 25, 30, 35, 40, 45, 50, 60, 70, 80, 90, 100, 150, 200, 250, 300, 350, 400, 450, 500, 600, 700, 800 or 900 μm, or about 1, 1.5, 2, 2.5, 3, 3.5, 4, 4.5 or 5 mm. In various embodiments of the invention the film may have a thickness in the range from about 15-60 µm, about 20-50 µm, or about 20-40 µm.

Films in accordance with the invention may have a tensile strength up to about 2 g/mm², for example, about 0.4 g/mm², about 0.5 g/mm², about 0.6 g/mm², about 0.7 g/mm², about 0.8 g/mm², about 0.9 g/mm², about 1.0 g/mm²; about 1.1 g/mm²; about 1.2 g/mm²; about 1.3 g/mm², about 1.4 g/mm²; about 1.5 g/mm²; about 1.6 g/mm²; about 1.7 g/mm²; about 1.8 g/mm², about 1.9 g/mm²; or about 2.0 g/mm².

In alternative embodiments of the invention, films according to the invention may have a tensile strength in a range from about 5 to about 50 KPa, for example, about 10 to about 40 KPa, about 12 to about 30 KPa, about 14 to about 25 KPa, about 15 to about 20 KPa, or about 16 to about 18 KPa, and may have a tensile strength of about 5, 10, 15, 20, 25, 30, 35, 40, 45 or 50 kPa.

The maximum load a film may be capable of bearing is related to the surface area of the film and may be calculated using methods known to those skilled in the art. For example, bioadhesive films according to the invention may be capable, of sustaining a load in the range from about 0.10 N to about 60N or from about 0.1 to 30, 0.1 to 10, 0.1 to 5, 0.1 to 1, 1 to 60, 10 to 60, 30 to 60, 1 to 30, 1 to 20, 5 to 20 or 10 to 20N, for example, about 0.1 N, about 0.2 N, about 0.3 N, about 0.4 N, about 0.5 N, about 0.6 N, about 0.75 N, about 1 N, about 3 N, about 5 N, about 10 N, about 20 N, about 30 N, about 40 N, about 50 N, or about 60 N.

The tensile strength of films according to the invention may be increased following irradiation with light. For example, a film may be 2-10 times as strong after irradiation in comparison with the tensile strength of the film prior to irradiation.

A film according to the invention may have a Young's modulus of between about 1 and about 20 MPa, or between about 1 and 15, 1 and 10, 1 and 5, 5 and 20, 10 and 20 or 5 and 10 MPa, and may have a Young's modulus of about 1, 2, 3, 4, 5, 6, 7, 8, 9, 10, 11, 12, 13, 14, 15, 16, 17, 18, 19 or 20 MPa. It may be flexed up to about 170° without suffering macroscopic damage, or up to 165, 160, 155, 150, 145, 140, 135, 130, 125 or 120°.

A film according to the present invention may have a water content of up to about 20% w/w, or up to about 15, 10 or 5% w/w, or between about 0 and about 20, 0 and 10, 0 and 5, 5 and 20, 10 and 20 or 10 and 15% w/w or about 0, 1, 2, 3, 4, 5, 6, 7, 8, 9, 10, 11, 12, 13, 14, 1, 5 16, 17, 18, 19 or 20% w/w. It may have a water contact angle of between 0 and 600, or between about 0 and 30, 0 and 10, 10 and 60, 30 and 60, 45 and 60, 30 and 50, 40 and 40 or 45 and 50°, and may have a water contact angle of about 0, 5, 10, 15, 20, 25, 30, 35, 40, 45, 50, 55 or 60°. It may be very hydrophilic, hydrophilic, moderately hydrophilic, somewhat hydrophilic or slightly hydrophilic.

Compositions according to the invention, including gels and films according to the present invention, may be substantially insoluble in water and physiological fluids. Gels and films according to the present invention may be insoluble in water or physiological fluids without or prior to treatment with a base, e.g. NaOH. A gel or film according to the invention may be treated with a base prior to use. The base may be an aqueous base, and may be for example aqueous sodium hydroxide, potassium hydroxide, ammonia or some other strong base. The base may be between about 1 and about 50% w/v, or between about 10 and 50, 20 and 50, 30 and 50, 40 and 50, 1 and 20, 1 and 10, 1 and 5, 5 and 40, 10 and 30 or 20 and 40%, and may be about 1, 2, 3, 4, 5, 10, 15, 20, 25, 30, 35, 40, 45 or 50% w/v. The treatment may be at room temperature, or it may be at between about 10 and about 40° C., or between about 10 and 30, 10 and 20, 20 and 40 or 15 and 25° C., and may be at about 10, 15, 20, 25, 30, 35 or 40° C., or may be at some other temperature. It may be for a time of between about 10 s and about 1 hour, or between about 10 s and 30 minutes, 10 s and 5 minutes, 10 s and 1 minute, 10 and 30 s, 30 s and 1 hour, 1 minute and 1 hour, 30 minutes and 1 hour, 1 and 30 minutes, 1 and 10 minutes or 1 and 5 minutes, and may be for about 10, 20, 30, 40 or 50 minutes, or 1, 2, 3, 4, 5, 10, 15, 20, 25, 30, 35, 40, 45, 50, 55 or 60 minutes, or for some other time. The treatment may comprise exposing the composition or film to the base, for example immersing the composition or film in the base or passing the base over the surface of the composition or base. Following the treatment with base, the gel or film may be washed with water or some other aqueous fluid in order to at least partially remove residual base on the surface of the gel or film. In one embodiment, the composition is substantially insoluble in water and physiological fluids prior to irradiation with light. In another embodiment, the composition is substantially insoluble in water and physiological fluids after irradiation with light. In other embodiments, bioadhesive compositions according to the present invention are not altered or degraded by aqueous solutions.

In further embodiments of the invention, compositions may include an agent which increases tensile strength and/or adhesion. For example, compositions according to the present invention may comprise an agent capable of increasing hydrogen-bonding within the composition, including for example a composition in the form of a bioadhesive film or gel, and tissue. In other embodiments, compositions according to the present invention may include an agent capable of increasing electrostatic interactions, for example, increasing polycationic-polyanionic bonding between the adhesive and tissue.

In alternative embodiments, compositions according to the present invention may include one or more cross-linking agents, for example, genipin, 4-vinylbenzoic acid, 4-vinylaniline, isocyanates, and carbodiimides e.g, 1-(3-dimethylaminopropyl)-3-ethylcarbodiimide (EDC). In some embodiments, the cross-linking agent may not be activable by UV light. In other embodiments, the cross-linking agent may not be activatable by blue light. The cross-linking agent may increase the amount of cross-linking within the polysaccharide. The cross-linking agent may increase the amount of cross-linking of the composition, including, for example, a composition in the form of a film or a gel, with tissue collagen. In other embodiments, compositions according to the present invention may not include a cross-linking agent.

Compositions according to the present invention may comprise one or more additives, for example a therapeutic agent. Examples of additives include wound healing agents, bacteriostats, antimicrobials, preservatives, antioxidants, antifungals and antibacterials. The concentration of the additive may depend on the nature and/or function of the additive, but may be for example in the range about 0.05 to about 2% w/w, or about 0.05 to 1, 0.05 to 0.5, 0.05 to 0.1, 0.1 to 2, 0.5 to 2, 1 to is 2, 0.1 to 1, 0.1 to 0.5 or 0.5 to 1% w/w, and may be about 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9 or 2% w/w. Suitable wound healing agents include phenyloin (diphenylhydantoin), 2'-deoxyribonucleosides, Platelet-Derived Growth Factor (PDGF), zinc etc.

According to a fourth aspect of the invention there is provided a process for preparing a light activatable bioadhesive composition comprising dissolving a polysaccharide and a light converter in an aqueous acidic solution, to produce said light activatable bioadhesive composition.

The process may comprise the use of one or more, for example 1, 2, 3, 4, 5 or more than 5, light converters. The process may comprise dissolving the polysaccharide in the aqueous acidic solution containing at least one of the one or more light converters, or it may comprise dissolving the polysaccharide in the aqueous acidic solution and then dissolving at least one of the one or more light converters in the aqueous acidic polysaccharide solution. Alternatively a solution of at least one light converter may be added to an aqueous acidic solution of the polysaccharide, or a solution of a second light converter may be added to an aqueous acidic solution of the polysaccharide and a first light converter. The solution of the at least one light converter, or of the second light converter, may be in a solvent. The solvent may be an organic solvent, and may be a solvent that is miscible with water. It may be a solvent that, in the concentration at which it is present in the composition, is not detrimental (e.g. irritating, corrosive, harmful, toxic) to tissue to which the composition is applied, or has negligible cytotoxicity. The solvent may be for example an alcohol, such as ethanol, methanol or isopropanol, or it may be some other solvent, for example acetone. The solution of the at least one light converter, or of the second light converter, may have a concentration such that the composition has a concentration of the light converter of about 0.01 to about 5 wt %, e.g. about 0.01 to about 4 wt %, about 0.01 to about 3 wt %, about 0.01 to about 2 wt %, about 0.01 to about 1 wt %, about 0.015 to about 1 wt %, about 0.02 to about 0.75 wt %, about 0.025 to about 0.7 wt %, about 0.03 to about 0.65 wt %, about 0.035 to about 0.6 wt %, about 0.04 to about 0.05 wt %%, and may be about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5 or 5 wt %. The solution of the at least one light converter, or of the second light converter, may have a concentration of between about 1 and about 20% w/v, or between about 1 and 10, 1 and 5, 1 and 2, 5 and 20, 10 and 20, 15 and 20, 5 and 15 or 8 and 12% w/v, and may have a concentration about 1, 2, 3, 4, 5, 6, 7, 8, 9, 10, 11, 12, 13, 14, 15, 16, 17, 18, 19 or 20% w/v. The concentration of the solvent in the composition may be less than about 2% w/v, or less than about 1.5 or 1%, or between about 0.1 and 2%, 0.5 and 2, 1 and 2, 0.1 and 1.5, 0.1 and 1, 0.1 and 0.5 or 0.5 and 1% w/v, and may be about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9 or 2% w/v In one embodiment, the light activatable bioadhesive composition is in the form of a gel.

Bioadhesive films according to the present invention may be prepared using processes known to those skilled in the art, including, solvent casting methods, thermal methods, compression moulding, extrusion, and the like.

According to a fifth aspect of the invention there is provided a process for preparing a light activatable bioadhesive film, said process comprising dissolving a polysaccharide and a light converter which is activatable by non-UV light in an aqueous acidic solution to produce a light activatable bioadhesive composition; and drying said bioadhesive composition to obtain said light activatable bioadhesive film.

The process according to the fourth or fifth aspect of the invention may optionally include a further step of treating said film or gel with one or more additives, for example a therapeutic agent, such that the film or gel becomes impregnated or coated with the one or more additives, e.g the therapeutic agent. In an alternative embodiment, an additive, for example a therapeutic agent, may be added to the acidic solution. Examples of additives include wound healing agents, bacteriostats, antimicrobials, preservatives, antioxidants, antifungals and antibacterials. The treating, or the adding to the solution, may be such that the additive is present in the film or gel in an effective concentration. The effective concentration may depend on the nature and/or function of the additive, but may be for example in the range about 0.05 to about 2% w/w, or about 0.05 to 1, 0.05 to 0.5, 0.05 to 0.1, 0.1 to 2, 0.5 to 2, 1 to 2, 0.1 to 1, 0.1 to 0.5 or 0.5 to 1% w/w, and may be about 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9 or 2% w/w.

Compositions, films and gels in accordance with the invention may comprise residual acid, including residual aqueous acid. For example, compositions, films and gels may comprise aqueous carboxylic acids such as acetic acid, formic acid, lactic acid, etc. In one form of the invention, a chitosan film or gel may comprise about 10 to about 14 wt % aqueous acetic acid.

In one embodiment the light activatable bioadhesive composition is spread over a plate, e.g., a perspex slide, then dried. In one embodiment, the composition is dried at room temperature. In one embodiment, the composition is dried at atmospheric pressure. In another embodiment the composition is dried in vacuum at a temperature in the range of about 0° C. to about 30° C., or between about 0 and 20, 0 and 10, 10 and 30, 20 and 30 or 10 and 20° C., for example about 4° C., about 5° C., about 10° C., about 15° C., about 20° C., about 25° C., about 30° C. The film can also be produced by the standard freeze-drying method.

With reference to the fourth or fifth aspect of the invention, the polysaccharide may be chitosan or chitin. The chitosan or chitin may be dissolved in the aqueous acidic solution at a concentration in the range of about 1% to about 20%. In another embodiment the concentration is about 1% to about 10%, or about 1% to 5%, 1% to 3%, 1% to 2%, 1.5% to 2.5%, 5% to 20%, 10% to 20% or 5% to 10%, for example, about 1%, about 2%, about 2.5%, about 3%, about 3.5%, about 4%, about 4.5%, about 5%, about 5.5%, about 6.0%, about 6.5%, about 7.0%, about 7.5%, about 8.0%, about 8.5%, about 9.0%, about 9.5% or about 10% w/w.

The acid may an organic acid or an inorganic acid. The organic acid may be a carboxylic acid or an amino acid. For example, the acid may be formic acid, acetic acid, trifluoroacetic acid, propionic acid, adipic acid, lactic acid, citric acid, malic acid, succinic acid, tartaric acid. Alternatively, the acid may be hydrochloric acid; sulfuric acid, phosphoric acid or nitric acid. In one embodiment the acid is acetic acid. The polysaccharide may form a salt following treatment with acid. The acid may be diluted with water. Alternatively the acid may be dissolved in water to prepare an acidic solution.

The acid may be present in an amount in the range from about 0.5% v/v to about 10% v/v, or between about 0.5 and 5, 0.5 and 2, 0.5 and 1, 1 and 10, 2 and 10, 5 and 10, 1 and 5 or 2 and 5% v/v, for example, about 0.5% v/v, about 1.0% v/v, about 1.5% v/v, about 2.0% v/v, about 2.5% v/v, about 3.0% v/v, about 3.5% v/v, about 4.0% v/v, about 4.5% v/v, about 5.0% v/v, about 5.5% v/v, about 6.0% v/v, about 6.5% v/v, about 7.0% v/v, about 7.5% v/v, about 8.0% v/v, about 8.5% v/v, about 9.0% v/v, or about 10% v/v.

The pH of the aqueous solution may be in the range from about 1 to about 6.5, or between about 1 and 6, 1 and 4, 1 and 2, 2 and 6.5, 4 and 6.5, 5.5 and 6.5, 2 and 6, 2 and 4 or 3 and 5, for example, pH of about 1, 1.5, 2, 2.5, 3, 3.5, 4, 4.5, 5, 5.5, 6 or 6.5. In one embodiment of the invention, the polysaccharide is chitosan and the pH is less than about 4.

The composition or film may be capable of adhering to tissue prior to illumination with non-UV light. The adhesive strength of the composition or film may be increased after illumination with non-UV light. The tensile strength of the film may be increased after illumination of non-UV light.

The wavelength of the light used to irradiate the composition or film may be selected according to the nature of the specific light activator(s). In one embodiment, the composition or film is irradiated with light having a wavelength ≥400 nm. The irradiation may comprise illumination. For example, the light may be visible or infrared light (including near-infrared, mid-infrared and far-infrared). In one embodiment, the light has a wavelength between about 750-850 nm, for example, 805-810 nm. In one embodiment, the light has a wavelength of 808 nm. Irradiation of the composition or film may be with non-UV light, and it may or may not also be with UV light.

The light may irradiate or illuminate the composition or film by moving a beam of the light across the composition or film. The speed may depend on the nature of the composition or film, the intensity of the beam and other factors. The speed may be for example between about 0.1 and about 10 mm/s, or between about 0.1 and 5, 0.1 and 1, 0.1 and 0.5, 0.5 and 10, 1 and 10, 5 and 10, 0.5 and 5, 0.5 and 2 or 0.8 and 1.2 mm/s, and may be about 0.1, 0.5, 1, 1.5, 2, 2.5, 3, 3.5, 4, 4.5, 5, 6, 7, 8, 9 or 10 mm/s. It may have a fluence of between about 20 and about 100 J/cm$^2$, or between about 20 and 80, 20 and 50, 40 and 100, 70 and 100, 30 and 60, 40 and 60 or 50 and 55 J/cm$^2$, and may be about 20, 30, 40, 45, 50, 55, 60, 65, 70, 75, 80, 90 or 100 J/cm$^2$, for example 50, 51, 52, 53, 54 or 55 J/cm$^2$. The power level may be between about 50 and about 200 mW, or between about 50 and 150, 50 and 100, 100 and 200, 100 and 150 or 150 and 200 mW, and may be about 50, 60, 70, 80, 90, 100, 110, 120, 130, 140, 150, 160, 170, 180, 190 or 200 mW. The irradiation time may depend on the power, the fluence, the nature and size of the composition or film etc. The irradiance may be between about 5 and about 50, or between about 10 and 50, 20 and 50, 5 and 20, 5 and 10 or 10 and 20 W/cm$^2$, for example about 5, 10, 15, 20, 25, 30, 35, 40, 45 or 50 W/cm$^2$. The resulting film or composition may display a maximum shear stress of greater than about 5 kPa, or greater than about 6, 7, 8, 9 or 10 kPa, or between about 5 and 50, 5 and 20, 5 and 10, 10 and 50, 10 and 20 or 10 and 30 kPa, for example about 5, 10, 15, 20, 25, 30, 35, 40, 45 or 50 kPa. During this time the temperature within the film may reach a maximum of about 70° C., or about 65, 60, 55, 50, 45, 40, 35, 35 or 25° C.

According to a sixth aspect of the invention there is provided a method for repairing a discontinuity in an area of tissue, said method comprising applying one or more light activatable bioadhesive films according to the third aspect of the invention to the tissue such that said area of tissue to be repaired is partially or fully covered by said one or more films; and irradiating said one or more films with non-UV light from a light source.

The step of irradiating may comprise illuminating said one or more films with non-UV light from a light source. If more than one (e.g. 2, 3, 4, 5, 6, 7, 8, 9, 10 or more than 10) films are used, they may be the same size and dimensions, or may be different sizes and/or dimension, or some may be the same and some maybe different.

In one embodiment, the area of tissue to be repaired is fully covered by said one or more films.

The method may further include the step of applying a bioadhesive gel according to the second aspect of the invention to an area of tissue near the site to be repaired prior to contacting said tissue with the bioadhesive film. In an alternative embodiment, the method includes the step of applying a bioadhesive gel according to the second aspect of the invention to a surface of the bioadhesive prior to contacting the bioadhesive film to said tissue.

According to a seventh aspect of the invention there is provided a method for repairing a discontinuity in an area of tissue, said method comprising applying a light activatable bioadhesive gel according to the invention to the tissue such that said area of tissue to be repaired is partially or fully covered by said gel; and irradiating said gel with non-UV light from a light source.

Irradiation of the gel with non-UV light may partially dehydrate the gel.

According to an eighth aspect of the invention there is provided a method of joining tissue, said method comprising aligning and abutting edges of the tissue to be joined, applying one or more light activatable bioadhesive films according to the third aspect of the invention so as to partially or fully cover said edges to be joined, and irradiating said one or more films with non-UV light from a light source.

With reference to the sixth or eighth aspects of the invention, when a plurality of bioadhesive films are used, the films may overlap with each other. Respective bioadhesive films may be the same or different. For example, respective films may differ in terms of their composition, size, shape, physical properties. Each film may, independently, have a width for example of between about 2 and about 10 mm, or between about 2 and 8, 2 and 6, 2 and 4, 4 and 10, 6 and 10, 4 and 6 or 4 and 5 mm, e.g. about 2, 2.5, 3, 3.5, 4, 4.5, 5, 5.5, 6, 6.5, 7, 7.5, 8, 8.5, 9, 9.5 or 10 mm, and a length of between about 5 and about 20 mm, or between about 5 and 15, 5 and 10, 10 and 20, 15 and 20, 10 and 15, 6 and 10 or 7 and 9 mm, e.g. about 5, 6, 7, 7.5, 8, 8.5, 9, 9.5, 10, 11, 12, 13, 14, 15, 16, 17, 18, 19 or 20 mm, or may have different dimensions to these.

With reference to the sixth or eighth aspects of the invention, the bioadhesive film may be used in conjunction with a light activatable gel according to the first or second aspect of the invention. The gel may function as a glue and may assist in sealing the area of tissue surrounding the site to be repaired or joined.

According to a ninth aspect of the invention there is provided a method of joining tissue, said method comprising aligning and abutting edges of the tissue to be joined, applying alight activatable bioadhesive gel according to the invention so as to partially or fully cover said edges to be joined, and irradiating said gel with non-UV light from a light source.

The tissue to be repaired or joined may be a nerve or blood vessel, e.g, an artery or vein, tissues of the genitourinary tract (e.g., ureter), lymphatic tubes, bile ducts, etc, wherein one or more films may be applied so as to partially or fully cover the area of tissue to be joined or repaired and one or more further films may be wound around said tissue. In one embodiment, a bioadhesive film according to the present invention may be configured as a stent. Examples of tissues/tubes that may be joined using bioadhesives according to the present invention are described in U.S. Pat. No. 6,583,117 (Lauto et al.), the entire contents of which are incorporated by cross-reference.

Illumination with non-UV light may increase adhesion between the film and the tissue.

The tissue may be mammalian tissue. The mammal may be human, non-human primate, murine, bovine, ovine, equine, caprine, leporine, avian, feline, porcine, or canine. The tissue may be internal or external. For example, the tissue may be selected from veins, arteries, microvessels, nerves, bone, cartilage, skin, cornea, organ tissues and surfaces (e.g, liver, intestine), biological surfaces such as peritoneum, pleura, dura mater and fascia The bioadhesive gel and/or film according to the invention may be used to seal a leak (eg, fluid or gas leak) or tear in a tissue, such as a vessel, organ, or biological surface. Bioadhesive gels and/or films according to the present invention may be used where urgent hemostasis is required.

The bioadhesive gel and/or film used in any of the sixth to ninth aspect of the invention may comprise a photoreactive group such as a UV-activatable group, for example a UV-activatable crosslinker. In this case the method may also comprise irradiating the gel and/or film with radiation of a wavelength suitable for activating the photoreactive group. The wavelength may be a UV wavelength. The irradiating may be for sufficient time and at sufficient intensity to cause the photoreactive group to react, for example to crosslink. The UV wavelength may be between about 200 and about 400 nm, or between about 250 and 400, 300 and 400, 350 and 400, 200 and 300, 200 and 250 or 250 and 350 nm, and may be about 200, 210, 220, 230, 240, 250, 260, 270, 280, 290, 300, 310, 320, 330, 340, 350, 360, 370, 380 or 390 nm wavelength. The irradiation by the UV wavelength may be before and/or after and/or at the same time as irradiation by non-UV light.

According to a tenth aspect of the invention there is provided a kit for repairing tissue, comprising a plurality of light activatable bioadhesive films and/or gels according to the invention. The films may independently differ in one or more of size, shape and area. The films and/or gels may be sterile. The kit may further comprise a light source, e.g., a laser or optical fibre. Films may be cut or configured according to the size, shape and area of the tissue/surface to be repaired.

According to an eleventh aspect of the invention there is provided a composition for the preparation of a bioadhesive composition, comprising a polysaccharide, a non-physiologically compatible reagent, and an energy converter.

The non-physiologically acceptable reagent may be an acid, such as an organic acid, or an aqueous acid. The organic acid may be a carboxylic acid, for example, acetic acid or aqueous acetic acid.

The non-physiologically acceptable reagent may be present in the composition in an amount in the range from about 4.5 wt % to about 18 wt %. The concentration of the energy converter in the composition or film may be about 0.01 to about 5 wt %, e.g. about 0.01 to about 4 wt %, about 0.01 to about 3 wt %, about 0.01 to about 2 wt %, about 0.01 to about 1 wt %, about 0.015 to about 1 wt %, about 0.02 to about 0.75 wt %, about 0.025 to about 0.7 wt %, about 0.03 to about 0.65 wt %, about 0.035 to about 0.6 wt %, about 0.04 to about 0.05 wt %. In particular, the energy converter may be present in an amount in the range about 0.2 wt % to about 0.5 wt %. The energy converter may be a light converter when the energy is in the form of light. The polysaccharide may be present in an amount in the range from about 81.09 wt % to about 95 wt %.

The composition may have a pH less than about 4, for example, less than about 3 or less than about 2, e.g. about 4, 3.5, 3, 2.5, 2, 1.5 or 1. In one embodiment, the polysaccharide is chitosan and the composition has a pH less than about 4, for example, less than about 3 or less than about 2.

According to a twelfth aspect of the invention there is provided a composition prepared by combining a non-water-soluble polysaccharide, an acidic medium, and an energy converter to form a mixture, and dehydrating the mixture to form the composition.

The composition may be a solid composition or a gelled composition.

The composition may comprise residual acidic medium after dehydration, for example, up to about 18 wt %.

Definitions

The following are some definitions that may be helpful in understanding the description of the present invention. These are intended as general definitions and should in no way limit the scope of the present invention to those terms alone, but are put forth for a better understanding of the following description.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

In the context of this specification the term "bioadhesive" refers to a substantially non-toxic biocompatible substance having adhesive properties which is capable of adhering to mammalian tissue.

In the context of this specification, the term "biomaterial" refers to any naturally occurring, naturally derived, or synthetic material or substance which is compatible with biological systems.

In the context of this specification, the term "chitosan" refers to an at least partially deacetylated product derived from chitin. The term "chitosan" should also be understood to include chitosan salts. The degree of deacetylation may vary and the term "chitosan" is not limited to a specific degree of deacetylation.

In the context of this specification, the term "degree of deacetylation" refers to the proportion of acetylamino groups in the 2-position of the carbohydrate units comprising the chitosan which have been converted to free amino groups, or salts thereof.

In the context of this specification, the term "film" should be understood to mean a solid film, wherein the film does not melt upon exposure to temperatures below 300° C., including temperatures below 250° C. Thus, films in the context of the present specification are distinguished from "solders" which denature, liquefy, melt or degrade at temperatures below 250° C.

In the context of this specification, the term "gel" includes gels and hydrogels.

In the context of this specification, the term "light converter" means a substance or a device which converts photons into heat or chemical energy. "Energy converter" also refers to a substance or a device which converts photons into heat or chemical energy.

The term "therapeutically effective amount" as used herein, includes within its meaning a sufficient amount a compound or composition of the invention to provide the desired therapeutic or diagnostic effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

Abbreviations

IG—indocyanin green
EDC—1-(3-Dimethylaminopropyl)-3-ethylcarbodiimide
TGA—Thermogravimetric analysis

BRIEF DESCRIPTION OF THE FIGURES

FIG. 6 is a histogram of viable cells (%) recovered from the extracted media, illustrating that more than 90% of recovered cells are still available after being treated with chitosan, while only 53% of cells appeared viable after ethanol incubation;

DETAILED DESCRIPTION OF PREFERRED EMBODIMENTS OF THE INVENTION

The present invention relates to a light activatable bioadhesive composition comprising a polysaccharide and an energy converter, for example a light converter, wherein the energy converter, or light converter, is activatable by non-UV light.

Compositions according to the present invention may be in the form of a film or a gel. The present invention also encompasses compositions in the form of a "pre-gel", which may be dehydrated to form a gel or a film. The present invention also relates to processes for preparing bioadhesive compositions, including bioadhesive gels and bioadhesive films. Films or gels according to the present invention may be useful for repairing or strengthening tissue or for joining discontinuous portions of tissue.

Bioadhesive compositions in accordance with the present invention comprise polysaccharides. Examples of polysaccharides which may be used in the present invention include aminopolysaccharides such as chitosan or chitin; heparin sulfate, chondroitin sulfate, beta-glucans, carrageenan, xantham gum, guar gum, locust bean gum, pectin, galactomannan, and acid polysaccharides such as hyaluronic acid and alginate. Bioadhesive compositions of the present invention may not comprise proteins, including blood derived proteins, such as albumin and fibrin.

The inventors have found that the addition of genepin to albumin based solders resulted in enhanced bonding strength. Despite this, the unique albumin/genepin solder remained soluble and brittle. Consequently, alternative biopolymers have been investigated in the design of a new tissue adhesive to overcome shortcomings of currently used solders.

Figure 1:
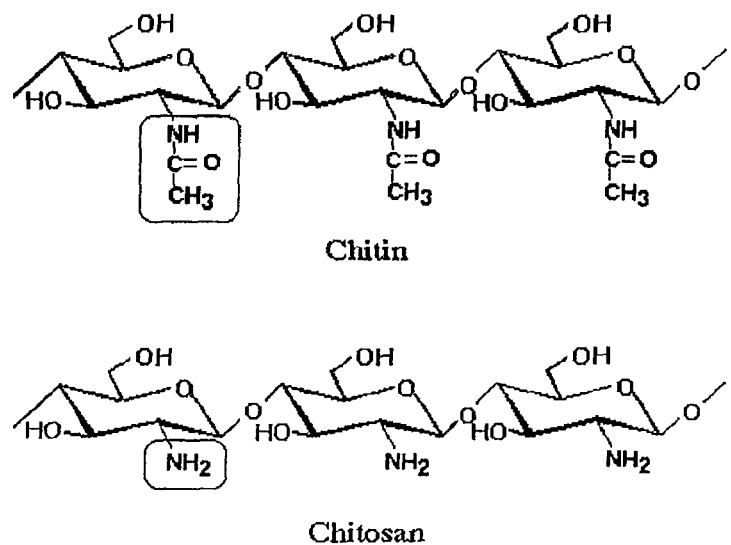
FIG. 1 shows the chemical structure of chitosan that is derived from deacetylated chitin.

Chitosan is a polysaccharide derived from deacetylated chitin and can be readily solvent cast in a film that has excellent mechanical properties and low toxicity (FIG. 1). Chitosan may also bind to collagen as demonstrated by previous studies, which reported polyanionic-polycationic and hydrogen bonding interaction between these two biopolymers. Previous investigators have shown that a pure polyanion-polycation complex is formed between the protein carboxylate group ($COO^-$) and the chitosan amino group ($NH_3^+$) when a solution of chitosan hydrochloride ($5*10^{-2}$ M) is added to a solution of collagen (1.7 g/l) with all its ionic sites fully dissociated (pH ~7.8). Such complex was insoluble in water and the polyanionic-polycationic interaction improved if the collagen was denatured by heat at 60° C. Further, a second mechanism of interaction occurred between chitosan and collagen when the polysaccharide exceeded the protein amount. FTIR analysis suggested hydrogen bonds formed between collagen molecules and chitosan amino groups. These complexes were also insoluble in water and circular dichroism spectra suggested that collagen was denatured.

In an attempt to improve bonding strength, other investigators have modified chitosan with lactobionic acid and p-azidebenzoic acid that was crosslinked with ultra-violet (UV) light a pig aorta defects. They observed a bursting pressure of ~30 KPa, significantly higher than the bursting pressure of specimens sealed with fibrin glue (~11 KPa). Histologic examinations of rabbit carotid arteries showed that 30 days after gel application in vivo, a fraction of the chitosan gel was phagocytosed by macrophages, partially degraded, and induced the formation of fibrous tissues around the gel. This chitosan gel was unfortunately water soluble prior to light crosslinking and therefore subject to fluid dilution like albumin solders.

The present inventors have developed a chitosan-based film without UV-crosslinker modifications. The novel film is insoluble, flexible and adheres firmly to tissue upon infrared laser activation.

One example of a polysaccharide which may be used in accordance with the present invention is chitosan (FIG. 1). Chitosan is a hydrophilic polymeric amine comprising glucosamine and N-acetylglucosamine. Chitosan has the chemical structure poly-(1-4)-2-amino-2-deoxy-β-D-glucose. Chitosan may be obtained by the deacetylation of chitin (poly-(1-4)-2-acetamino-2-deoxy-β-D-glucose). The degree of acetylation of the amine group(s) may modified to adjust the structural properties of chitosan. Chitosan contains free amino groups, one or more of which may be protonated by acid to form ammonium ions and salts.

The mechanical properties and rate of degradation of chitosan-derived bioadhesive compositions may be modified by controlling or manipulating the degree of acetylation. The degree of acetylation of chitosan may be between about 0% and about 95%, or from about 25% to about 95%, or from about 0% to about 90%, or from about 0 to 70, 0 to 50, 0 to 30, 0 to 10, 20 to 90, 40 to 90, 60 to 90, 10 to 80, 30 to 60 or 40 to 60%. In various embodiments of the present invention, the degree of acetylation is about 0%, about 5%, about 10%, about 15%, about 20%, about 25%, 30%, about 35%, about 40%, about 45%, about 50%, about 55%, about 60%, about 65%, about 70%, about 75%, about 80%, about 85%, about 90% or about 95%. Generally, the greater the degree of deacetylation the faster the rate of degradation. The degree of deacetylation of chitosan may be calculated as described by Khan et al (*J. Pharm. Pharmaceut. Sci* 3(3):303-311, 2000), the entire contents of which is incorporated herein by cross-reference.

In one embodiment of a composition according to the present invention, the polysaccharide may not modified, eg, the polysaccharide is not covalently functionalised with a UV-activatable group, including a UV-activatable crosslinker. In alternative embodiments of a composition according to the present invention, the polysaccharide may be modified (e.g. with a photoinitiator group), wherein the composition may further comprise a non-physiologically compatible reagent, such as an acid.

Bioadhesive gels and films according to the present invention may adhere to a tissue surface through one or more mechanisms including, cross-linking, electrostatic interaction, hydrogen bonding, and mechanical interlocking (eg, arising from textured surface morphology of the tissue and/or film or gel).

Compositions according to the present invention comprise an energy converter, such as for example a light converter, which is activatable by non-UV light, e.g. visible light, or near-, far-, or mid-infrared light. When the composition, including for example the composition in the form of a gel or a film, is illuminated with non-UV light from a light source such as a laser, the energy converter, or light converter, converts light energy of the non-UV light into other forms of energy (e.g. heat energy, chemical energy), which may result in an increase in the tensile strength and adhesiveness of the composition due to cross-linking of the polysaccharide. Thus an energy converter which is activatable by non-UV light is capable of absorbing the non-UV light and/or converting the non-UV is light into the other forms of energy. Irradiation of the energy converter, e.g. light converter, with light of suitable wavelength may also promote cross-linking between the polysaccharide and components of tissue (eg, collagen) to which composition is adhered. Use of non-UV light may prevent thermal damage to tissue.

The energy converter, or light converter, may be a dye, such as for example, a genipin dye, squid ink, melanin, or indocyanine green (IG). In one embodiment, the dye is indocyanine green (IG). IG strongly absorbs radiation at 808 nm and converts photons into heat, which is transferred to the adhesive and tissue interface and promotes bonding. In other embodiments, the energy converter may be an initiator for radical polymerisation, such as carboxylated camphorquinone. Upon irradiation with visible (blue) light, carboxylated camphorquinone may photoinitiate cross-linking of a reactive species, such as 4-vinylbenzoic acid, which has been previously added to the polysaccharide (e.g, chitosan) and promote crosslinking of the polysaccharide and/or tissue. Exposure of the composition (e.g, film or gel) to non-UV light may also result in increased mechanical bonding of the film or gel to tissue with which the gel or film is in contact, including, for example, facilitating hydrogen bonding, covalent bonding, electrostatic interactions (eg, polycationic-polyanionic interactions), or cross-linking between the polysaccharide in the composition and collagen in the tissue.

Bioadhesive films and gels according to the present invention may be used separately, or in combination, to achieve mechanical closure of tears, holes, incisions, etc, in tissue. Bioadhesive gels and films according to the invention may also be used to strengthen tissue or form a seal over a tear, hole, incision, leak etc. In some embodiments of the invention, bioadhesive films according to the present invention may be useful for mechanically joining and/or sealing a tissue site and, for example, may reduce or prevent fluid and/or gas release or diffusion from a tissue site.

Bioadhesive films in accordance with the present invention have tensile strength and flexibility such that they may be suitable for use in tissue repair. Bioadhesive films according to the present invention may have a degree of flexibility, which allows the films to be manipulated, e.g, bent, twisted, or stretched, without substantial breakage; Bioadhesive films and gels according to the present invention suitably may have adhesive strength >about 20 kPa. The adhesive strength may be greater than about 5, 10, 15, 20, 25 or 30 kPa, and may be about 5, 10, 15, 20, 25 or 30 or more than 30 kPa. Bioadhesive films and gels according to the present invention may be used as sealants and suitably may have a burst pressure >about 40 mmHg. The burst pressure may be greater than about 20 mmHg, or greater than about 25, 30, 35, 40, 45, 50, 55 or 60 mmHg, and may be about 20, 25, 30, 35, 40, 45, 50, 55, 60 or more than 60 mmHg.

Bioadhesive films according to the invention can be prepared using processes known by is those skilled in the art, including, for example, solvent casting methods, spin coating, thermal processes, and extrusion processes.

For example, spin coating is a technique by which very thin films are deposited onto a solid substrate. To fabricate thin polymer films, a polymer is first dissolved in a volatile solvent (e.g. acetic acid). If a drop of solution is placed on a substrate, it can flow to form a metastable, continuous film or form a droplet on the surface, depending on the "wettability" of the substrate. By spinning the substrate, the droplet is forced to spread out while the solvent evaporates. If deposition conditions such as choice of solvent, solution concentration and spin speed are chosen correctly, a thin film of uniform thickness is deposited on the substrate.

Polymer extrusion involves the conversion of a raw material, usually in the form of a molten state polymer, into a finished product or part by forcing it through an opening. The process comprises pumping a molten state polymer, under pressure, through a die, producing a continuous cross section or profile. For continuous extrusion the pumping action is typically performed by a screw inside a barrel or a combination of screws. The polymers used are typically thermoplastics and are melted by heating the barrel. The opening in the die is the guide after which the extrudate takes its final form.

In some embodiments of the invention the composition may further comprise an agent which increases film tensile strength and/or adhesion. For example, compositions according to the present invention, including compositions in the form of gels or films, may include one or more agents which are capable of increasing the amount of hydrogen bonding between the gel or film and tissue collagen, and/or may increase the electrostatic interaction between the gel or film and tissue collagen; and/or may increase mechanical bonding between the gel or film and tissue collagen. Examples of an agent which may increase tensile strength and/or adhesion is a cross-linking agent, such as, alginate, hydroxyapatite, and chondroitin sulfate.

Bioadhesive films according to the invention may comprise one or a plurality of, e.g. 1, 2, 3, 4, 5, 6, 7, 8, 9, 10 or more than 10 film layers, wherein respective layers may be the same or different. For example, individual film layers may comprise the same or different energy converters and/or light converters and may independently comprise additional agents, such as therapeutic agents, and/or agents which increase tensile strength. In one embodiment, the film is multilayered. In another embodiment, the film comprises a single layer. In the case of multiple layers, there may or may not be bioadhesive gel between any two of the layers.

Compositions of the invention, including compositions in the form of bioadhesive films or gels, may also function as drug delivery systems to deliver therapeutic agent(s) to a tissue repair site. For example, a bioadhesive film may be attached to a drug delivery medium. The film may be attached to a drug delivery medium before or after irradiation with non-UV light. In alternative embodiments, bioadhesive films according to the invention may be used in conjunction with bioadhesive gel compositions, including bioadhesive gels according to the invention. The film, gel, or both, may comprise one or more therapeutic agents or other additives. Examples of therapeutic agents include antibiotics; antifungal agents; nucleic acids (e.g, RNA, DNA, including cDNA); proteins, including proteins within a delivery vehicle such as a liposome, or virus; enzymes; enzyme inhibitors; growth factors, haemostatic agents, anti-inflammatory agents, anaesthetics; thrombolytics; thrombogenics, etc. The therapeutic agent may be added to the bioadhesive film and/or gel prior to application to tissue. The therapeutic agent may be added prior to or after irradiation of film and/or gel with light. The therapeutic agent may be incorporated within the bioadhesive film and/or gel. Alternatively, the therapeutic agent may coat or partially coat one or more surfaces of the bioadhesive film and/or gel.

In another embodiment of the invention, the bioadhesive film and/or gel may comprise an enzyme to promote degradation of the bioadhesive film and/or gel in situ.

Compositions of the invention, including compositions in the form of bioadhesive films or gels, may also function as drug delivery systems to deliver therapeutic agent(s) to a tissue repair site. For example, compositions, films or gels according to the present invention may further comprise one or more therapeutic drugs, such as, for example, antibiotics; antifungal agents; nucleic acids (e.g. RNA, DNA, including cDNA); proteins, including proteins within a delivery vehicle such as a liposome, or virus; enzymes; enzyme inhibitors;

growth factors, haemostatic agents, anti-inflammatory agents, anaesthetics, thrombolytic agents, thrombogenics agents, etc. The therapeutic agent(s) may assist or promote wound healing.

Compositions, including films and gels in accordance with the present invention may also be used concurrently with other therapies or therapeutic regimes to reduce the risk of infection and/or to promote healing.

Bioadhesive films according to the present invention may be prepared or cut into any size and shape as required and to suit the tissue to which the films are to be adhered. For example, a bioadhesive film may be substantially planar, or may be formed into a tubular or cylindrical structure having an appropriate cross-section suitable for the intended use. Bioadhesive films of different thickness may also be prepared and used according to need.

Bioadhesive films and gels according to the present invention may be useful for tissue repair due to their mechanical properties such as flexibility, modulus (tensile strength) and adhesive strength. Bioadhesive films according to the present invention may be resilient such that they may be capable of returning to a previous conformation after being bent or twisted. In addition, bioadhesive films according to the present invention may be configured to enable application with a surgical instrument, such as an endoscope. In one embodiment, a bioadhesive film according to the invention may be used as a stent.

Light activatable bioadhesive compositions, including gels and films according to the present invention may be useful in surgical procedures, for example, procedures where access to a tissue to be repaired may be restricted, such as, for example, laparoscopic, endoscopic and microsurgical procedures. Light activatable bioadhesive compositions, including gels and films according to the present invention may be used in conjunction with surgical devices, including for example endoscopy devices through which an optical fibre may be used as a light source to reach the repair site and illuminate light of a suitable wavelength on the gel or film.

In one embodiment of the invention, one or more bioadhesive films may be placed over an area of tissue to be repaired. The films may be arranged in any suitable manner so as to fully or partially cover the area of tissue to be repaired, as appropriate. In addition, multilayer films may be used. The bioadhesive film(s) is capable of initially adhering to tissue with which it is in contact.

Once positioned in contact with an area of tissue, the film(s) may be illuminated with non-UV light from a light source. Examples of suitable light sources include include diode lasers, e.g, GaAlAs diode lasers, Nd:YAG lasers, Argon lasers, Holmium:Yag lasers, Erbium:Yag lasers and $CO_2$ lasers. The laser may be coupled with an optical fibre, e.g., a multimode optical fibre. The laser may also be coupled with a laser scanner to expedite and improve the beam delivery. Illumination with light of a suitable wavelength may be performed constantly or intermittently. If more than one light converter is present in the film or plurality of films, illumination with light of different wavelengths may be performed. Illumination may continue for as long as necessary to achieve sufficient adhesion suitable for the procedure. A laser may deliver trains of short pulses lasting for as long as nanoseconds, microseconds or milliseconds, as appropriate. For example, illumination may be applied constantly or intermittently for a period of time in the range from about 5 seconds to about 5 mins, such as about 10 sec, about 20 sec, about 30 sec, about 40 sec, about 50 sec, about 60 sec, about 70 sec, about 80 sec, about 90 sec, about 100 sec, about 110 sec, about 120 sec, about 130 sec, about 140 sec, about 150 sec, about 160 sec, about 170 sec, about 180 sec, about 200 sec, about 210 sec, about 220 sec, about 230 sec, about 240 sec, about 250 sec, about 260 sec, about 270 sec, about 280 sec, about 300 sec.

The film(s) may achieve a shear stress of the adhesive bond to tissue to which it is bonded (for example to a nerve) of at least about 2 kPa, or at least about 5, 10, 15 or 20 kPa, or between about 2 and 50 kPa, 2 and 30, 2 and 20, 2 and 10, 5 and 50, 10 and 50, 20 and 50, 5 and 30, 10 and 30 or 10 and 20 kPa, or of about 2, 3, 4, 5, 6, 7, 8, 9, 10, 11, 12, 13, 14, 15, 16, 17, 18, 19, 20, 25, 30, 35, 40, 45 or 50 kPa.

Illumination with non-UV light may increase the tensile strength of the bioadhesive film(s) and gels. Illumination with non-UV light may increase the adhesiveness of the bioadhesive film(s) and gels. The illumination may be of sufficient intensity and for sufficient time that the tensile strength and/or adhesiveness of the film(s) and/or adhesive is increased to a level where the film and/or gel is usable for repairing a discontinuity in an area of tissue. Because the bioadhesive films of the present invention are comprised of polysaccharides they may be degraded in situ over a period of time. The bioadhesive films, gels and degradation products thereof are suitably non-toxic to mammals.

Light-activatable bioadhesive compositions, including films and gels, according to the present invention are substantially insoluble in aqueous solution, including physiological solutions. Bioadhesive compositions according to the present invention may not need to be treated with a basic solution (eg, NaOH) in order to become substantially insoluble in aqueous solution.

In accordance with one embodiment of the present invention, a bioadhesive film of ~20 µm thickness may sustain a load of ~0.50 N without breaking, may be bent, e.g. to −160 degrees without breaking or tearing, and furthermore may return to the initial shape with no macroscopic sign of damage.

In other embodiments described herein, films according to the present invention may be used with a light activatable bioadhesive composition according to the invention which is in the form of a gel. The gel may function as a "glue" to assist adhesion of a bioadhesive film or to assist in the formation of a seal (e.g. which may be fluid and/or gas impervious) over the tissue repair site. Other bioadhesive gels, such as protein based gels, e.g., albumin and fibrin bioadhesive gels, may be used in conjunction with films according to the present invention.

The bioadhesive gels and/or films of the present invention may be used for repairing a discontinuity in an area of tissue. A discontinuity in this context may be for example a tear, hole, incision, leak, cut, a lesion, a graze, a cavity or some other type of discontinuity. One or more light activatable bioadhesive films according the invention may be applied to the tissue such that said area of tissue to be repaired is partially or fully covered by said one or more films. The films may at least partially overlap, or may be layered, or may not overlap, in order to increase either the area of repair, or the strength of the repair, or both. The film(s) may then be irradiated with non-UV light from a light source. A bioadhesive gel according to the invention may be applied to an area of tissue near the site to be repaired prior to contacting said tissue with the bioadhesive film. This may provide additional reinforcement for the repair. Alternatively, the bioadhesive gel may be applied to the bioadhesive film prior to applying the film to the area to be repaired.

The method for repairing a discontinuity in an area of tissue may therefore comprise one or more of the following methods:

A) applying one or more light activatable bioadhesive films according to the invention to the tissue such that said area of tissue to be repaired is partially or fully covered by said one or more films; and irradiating or illuminating said one or more films with non-UV light from a light source;
B) applying a bioadhesive gel according to the invention to an area of tissue near the site to be repaired; applying one or more light activatable bioadhesive films according to the invention to the tissue, or to the gel, such that said area of tissue to be repaired is partially or fully covered by said one or more films and/or by the gel; and irradiating or illuminating said one or more films and the gel with non-UV light from a light source;
C) applying a bioadhesive gel according to the invention to one or more bioadhesive films according to the invention; applying the one or more films, together with the gel, to the area to be repaired to the tissue such that said area of tissue to be repaired is partially or fully covered by said one or more films; and irradiating or illuminating said one or more films with non-UV light from a light source. The film may be applied to the tissue such that the film is in contact with the tissue, or such that the gel is in contact with the tissue, or such that both the gel and the film are in contact with the tissue.

As a further alternative, the repair may be effected by applying a light activatable bioadhesive gel according to the invention to the tissue such that said area of tissue to be repaired is partially or fully covered by said gel. The gel may be then irradiated or illuminated with non-UV light from a light source, as described above. The irradiation or illumination of the gel may partially dehydrate the gel. It may for example remove up to about 20% of the water in the gel, or up to about 30, 40, 50, 60, 70, 80 or 90% of the water in the gel.

Various options may be employed for using the gel and/or film of the present invention for repair or joining of tissue. For example alternating layers of gel and film may be used in order to reinforce the repair with a gel-film assembly. Thus a first layer of gel may be applied to part or all of the tissue to be repaired or of the parts to be joined, and a first film applied to the first layer of gel. A second layer of gel may be applied to part or all (for example around part or all of the periphery) of the first film and a second film applied to the second layer of gel. Further layers of gel and film may be added to the above assembly using the same process (i.e. applying a subsequent layer of gel to part or all of the previous film and applying a subsequent film to the subsequent layer of gel). The entire assembly may then be illuminated with non-UV light. Alternatively, one or more components of the assembly may be illuminated with non-UV light prior to complete assembly, and thereafter the entire assembly may be illuminated with non-UV light.

In a variation, a first layer of gel may be applied to part or all of a first film, and the first film, with the first layer of gel applied to part or all of the tissue to be repaired or of the parts to be joined. It may be applied so that the first layer of gel contacts at least a part of the tissue to be repaired or of the parts to be joined. A second layer of gel may be applied to part or all (for example around part or all of the periphery) of a second film and the second film, with the second layer of gel, applied to the first film. The second layer of gel may contact the first film. Further layers of gel and film may be added to the above assembly using the same process (i.e. applying a layer of gel to part or all of a film, and applying the second film, with the second layer of gel, to the film). There may be a total of 1, 2, 3, 4, 5, 6, 7, 8, 9, 10 or more than 10 films in a gel-film assembly. Each film may be the same size or different size relative to any other film. The entire assembly may then be illuminated with non-UV light. Alternatively, one or more components of the assembly may be illuminated with non-UV light prior to complete assembly, and thereafter the entire assembly may be illuminated with non-UV light.

In a further variation, a wound healing agent may be used in conjunction with a film, and optionally a gel, according to the present invention. Thus the wound healing agent may be applied to at least part of a wound, e.g. the tissue to be repaired or to the parts to be joined. The film may then be applied over the wound healing agent so that it contacts a part of the tissue and covers the wound healing agent. The film may then be illuminated with non-UV light. Alternatively a film according to the invention may have the wound healing agent applied to a centre portion thereof, and optionally a gel applied to a peripheral portion thereof, on the same side as the wound healing agent, and the film applied to the wound or join such that the wound healing agent contacts at least part of the wound or join. The film may then be illuminated with non-UV light. The wound healing agent may be any of the wound healing agents known in the art.

Figure 21:
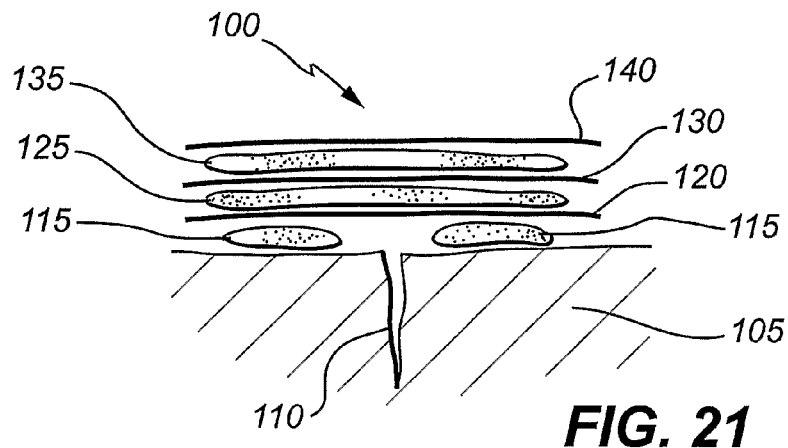
FIG. 21 shows a diagrammatic representation of the repair of a lesion by film and gel according to the present invention, in which multiple layers of film are used.

FIG. 21 shows a gel-film assembly made as described above. In FIG. 21, assembly 100 is used for repair of tissue 105, having lesion 110. In assembly 100, first gel layer 115 is in contact with a portion of tissue 105 surrounding lesion 110, and assists in adhering first film 120 to tissue 105. Second gel layer 125 is located between first film 120 and second film 130, and third gel layer 135 is located between second film 130 and third film 140. Illumination of assembly 100 with non-UV light activates gels 115, 125 and 135 and also activates films 120, 130 and 140 in order to improve adhesion of assembly 100 to tissue 105 and adhesion of films 120, 130 and 140 to each other. In assembling assembly 100, one option is to apply gel layer 115 to tissue 105, then apply film 120 to gel layer 115, then apply gel layer 125 to film 120, then apply film 130 to gel layer 125, then apply gel layer 135 to film 130 and finally apply film 140 to gel layer 135. Alternatively, gel layer 115 may initially be applied to film 120, and film 120 applied to tissue 105 such that gel layer 115 contacts tissue 105. The remainder of assembly 100 may then be assembled as described above. Alternatively, gel layer 125 may be applied to film 130 and film 130 applied to film 120 such that gel layer 125 contacts film 120. Then gel layer 135 may be applied to film 140, and film 140 applied to film 130 such that gel layer 135 contacts film 130. The entire assembly may then be illuminated with non-UV light. Alternatively, one or more components of the assembly may be illuminated with non-UV light prior to complete assembly, and thereafter the entire assembly may be illuminated with non-UV light.

In another option for using the gel and film of the present invention for repair or joining of tissue, gel may be applied to either side of a fissure, crack split or cut in a tissue, or to each of two parts of tissue to be joined, and a film applied to the gel, after which the area to be repaired may be illuminated with non-UV light.

In another option, a film may be applied to at least a part of an area of tissue to be repaired or to each of two parts of tissue to be joined. Gel may be used to seal around the periphery of the tissue, and the area illuminated with non-UV light.

In yet another option, a first film, optionally with gel, may be applied to the area of tissue to be repaired (or to the aligned parts to be joined), and a second film, optionally with gel between the first and second film, may be applied in order to cover or encapsulate the first film. The second film may be larger than the first film, and the periphery of the second film may contact the tissue to be repaired, or the parts to be repaired. The second film may have gel around its periphery in order to seal a gap between the second film and the tissue. The area may then be illuminated with non-UV light.

The films and/or gels of the present inventions may be used for repairing nerves, or other thin elongated structures. In this case a film used for repairing the nerve or other structure may wrap around the nerve or other structure. In that case a first portion of the film may adhere to a second portion of the film. This may be accomplished such that a portion of a first side of the film adheres to another portion of the first side, or such that a portion of a first side of the film adheres to a portion of the second side. The adhesion may or may not be accomplished at least in part by means of gel. Activation of the film by illumination by non-UV light may be performed before or after the film is applied to the nerve or other structure. Activation of the gel may be performed after application of the film to the nerve or other structure. Thus a film may be prepared and activated by illumination with non-UV light, then gel applied to the film, and the film plus gel applied as described above to the nerve or other structure. Activation of the gel with non-UV light may then improve the adhesion and/or physical properties of the gel, and therefore of the entire assembly. Alternatively gel may be applied to an unactivated film, and the gel plus film applied to the nerve or other structure as described above. Illumination with non-UV light may then activate both the film and the gel in order to improve adhesion and/or physical properties of the gel and the film.

Other options for using the gel and film of the present invention will be readily apparent to one skilled in the art.

When applying the film to an area to be repaired, or to two parts to be joined, it may be advantageous to use mechanical means to locate the film and to maintain it in place. Such mechanical means may include ties, wraps, covers, pins, clamps, clips etc. These may be retained in place before and/or during illumination of the film with non-UV light. They may or may not be removed after the illumination.

Figure 22:
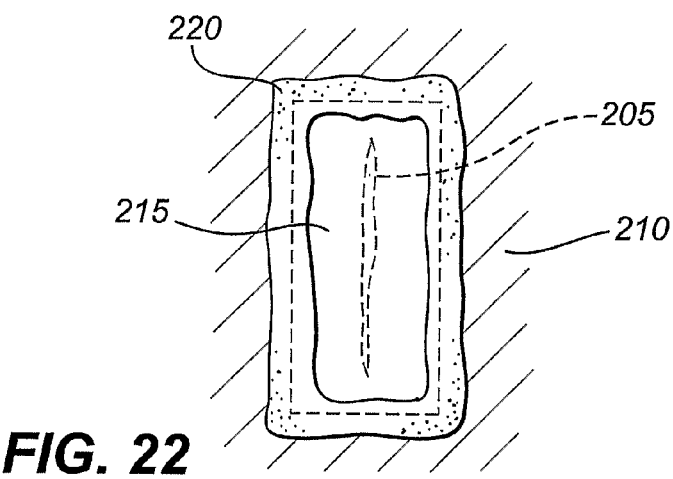
FIG. 22 shows a diagrammatic representation of the repair of a lesion by film and gel according to the present invention, in which a film is sealed around at least a part of its periphery by gel.

FIG. 22 shows another option for using the gel and film of the present invention. In FIG. 22, lesion 205 in tissue 210 has been repaired by film 215 and gel 220. Thus film 215 has been applied to tissue 210 so as to completely cover lesion 205. Gel 220 has been applied to the periphery of film 215, and extending so as to contact tissue 210 near the periphery of film 215, so as to seal between the edges of film 215 and tissue 210. Illumination of film 210 and gel 215 with non-UV light activates them in order to improve adhesion and physical strength.

Figure 23:
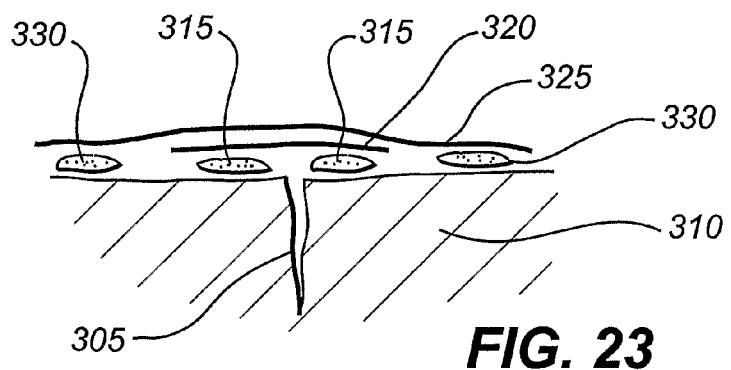
FIG. 23 shows a diagrammatic representation of the repair of a lesion by film and gel according to the present invention, in which a film is covered by a larger film.

FIG. 23 shows still another option for using the gel and film of the present invention. In FIG. 23, which shows a side view, lesion 305 is present in tissue 310. First gel layer 315 is present in contact with a part of tissue 310 near lesion 305, and serves to adhere first film 320 to tissue 310. Second film 325 is larger than first film 320, and covers film 320. Second film 325 is adhered to tissue 310 by means of gel layer 330, such that gel layer 330 at least partially surrounds first film 320.

Figure 24:
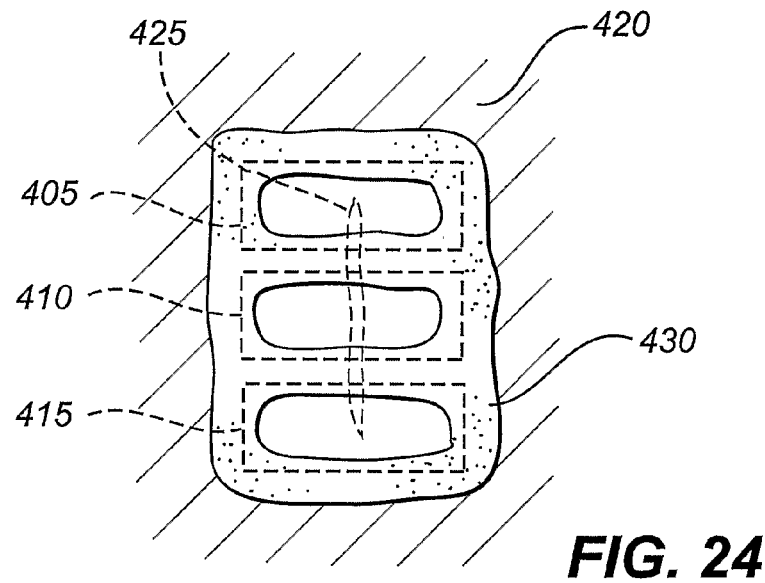
FIG. 24 shows a diagrammatic representation of the repair of a lesion by film and gel according to the present invention, in which several films are used but do not overlap.

FIG. 24 shows a further option for using the gel and film of the present invention. In FIG. 24, films 405, 410 and 415 are applied to tissue 420 in order to repair lesion 425 in tissue 420. Gel 430 is provided surrounding the peripheries of films 405, 410 and 415 so as to seal between the peripheries of films 405, 410 and 415 and tissue 420, and ensure that lesion 425 is correctly repaired.

Figure 25:
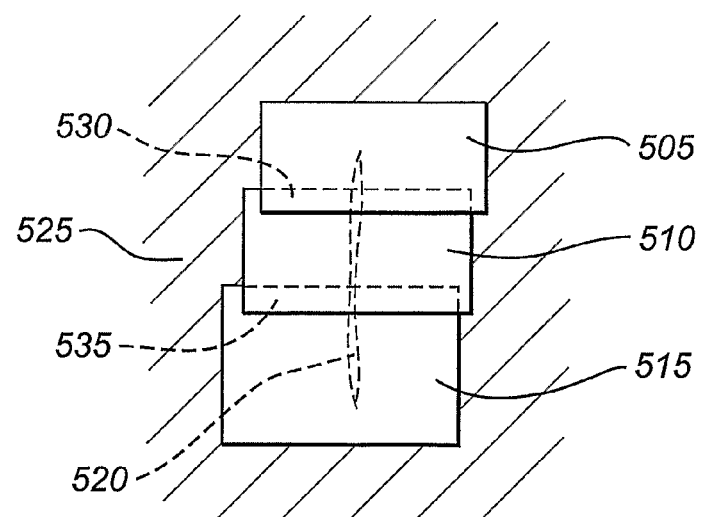
FIG. 25 shows a diagrammatic representation of the repair of a lesion by film according to the present invention, in which films overlap.

FIG. 25 shows yet a further option for using the film of the present invention. In FIG. 25, films 505, 510 and 515 are used to repair lesion 520 in tissue 525. Films 505, 510 and 515 partially overlap each other i.e. film 505 partially overlaps film 510 in overlap region 530 and film 510 partially overlaps film 515 in overlap region 535. Each film contacts a part of tissue 525, and spans a part of lesion 520 such that all parts of lesion 520 are spanned by at least one of the films.

The gel may be suitable for the repair or join of organs/tissues having an irregular surface, such as a damaged liver or lung. Bioadhesive films may be suitable for use on tissues/organs with relatively smooth surfaces, such as nerves, dura mater, bones, muscles, peritoneum. Nevertheless, chitosan films may also be used for the repair of organs/tissue having an irregular surface, such as a lung or a liver. The use of a bioadhesive film may provide a stronger repair than use of the gel alone, as the illuminated film may be cohesively stronger than the illuminated gel. When the gel is thermally activated, more energy is required to evaporate water compared to the film, as the gel typically has a higher water content than the gel. This may lead to a greater degree of thermal damage to surrounding tissue when using the gel, relative to using the film. On the other hand, if the gel or film is photoactivated, i.e. activated by light of a wavelength outside the thermal, or infra-red, range, it may not induce any thermal damage.

Thus the repair may be effected using gel, film or both. The irradiation may increase adhesion between the film and/or gel and the tissue being repaired. It may also improve the physical properties (e.g. tensile strength) of the film and/or gel, thereby improving the repair.

The discontinuity to be repaired may comprise a gap between two portions of tissue to be joined. In this case, the process of repairing the discontinuity may represent joining tissue, i.e. joining the two portions of tissue. It will be understood that the method could be used to join more than two portions of tissue, e.g. 3, 4, 5 or more than 5 portions of tissue, and that the joining may be conducted in a single step (i.e. with a single irradiation step) or in more than one step (i.e. with more than one irradiation step). If two or more portions of tissue are to be joined, they may be aligned prior to application of the film and/or gel, or prior to irradiation of the film and/or gel, in the configuration in which they are desired to be joined. For example edges of the portions may be aligned and/or abutted.

As described above, the film of the present invention may be used in conjunction with a light activatable gel according to the invention, by applying the gel either to the film or to the tissue to be repaired and/or joined or to both. The gel may function as a glue and may assist in sealing the area of tissue surrounding the site to be repaired and/or joined.

EXAMPLES

The invention will now be described in more detail, by way of illustration only, with respect to the following examples. The examples are intended to serve to illustrate this invention and should not be construed as limiting the generality of the disclosure of the description throughout this specification.

Example 1

Preparation of Chitosan Adhesive Film

In the first experimental group (Group I), deacetylated chitosan (≥85%) from crab shells (Sigma, St. Louis, Mo., USA) was dissolved to a concentration of 2% w/v in a water solution containing acetic acid (2% v/v) and indocyanine green (IG, 0.02% w/v).

In the second experimental group (Group II), the chitosan solution of group I was prepared without the dye Indocyanine Green (IG).

In the third experimental group (Group III), an ethanol solution of genipin (10% w/v) was added to the green chitosan gel of the first group to obtain final concentrations of 1% (w/v) genipin and 0.7% (v/v) ethanol.

In the fourth experimental group (Group IV), a genipin-chitosan solution was prepared as in group III but without IG dye.

All gelatinous chitosan solutions (pH ~4.0) were stirred for 6 hours at 4° C. before spreading evenly (thickness ~2 mm, surface area ~12 cm$^2$) over a sterile and dry, perspex plate. The chitosan solutions were then dried for ~6 days under clean conditions and atmospheric pressure at 4° C. It should be noted that drying temperatures of up to room temperature (e.g. between about 0 and about 25° C., or between about 0 and 20, 0 and 15, 0 and 10, 0 and 5, 5 and 25, 10 and 25 or 5 and 10° C., for example, about 0, 5, 10, 15, 20 or 25° C.) may be used, however drying at 4° C. provided better results than room temperature drying. The resulting chitosan films were carefully detached from the plate without damage and were insoluble in water. A digital caliper was used to measure the adhesive thickness, which ranged from 15 to 30 µm. All films were thereafter cut in rectangular strips (~7.5×4.5 mm), placed between sterile glass slides to preserve their flat shape and stored in the dark at 4° C.

Genipin was added to the chitosan solution in order to explore a possible enhancement of film adhesion to tissue, as previously demonstrated for albumin solders. The final concentrations of genipin (1%) and ethanol (~0.7%) were suggested by previous studies. Further, 0.7% of ethanol likely induces negligible cytotoxicity.

In the following experiments, statistical comparison of means was made using the two-tails unpaired Student's t-test, ANOVA one-way and Bonferroni's multiple comparison test at 0.05 level of significance.

Example 2

Adhesive Attenuation

A UV-Visible spectrophotometer was used to measure the laser attenuation at 808 nm within the films and to observe the attenuation characteristics of the adhesive due to the presence of IG and genipin. The wavelength of 808 nm corresponds to the absorption peak of IG and to the laser radiation used for laser tissue repair. Adhesive films were fixed inside a plastic cuvette and placed in the light beam, which scanned the adhesives at the wavelength range of 400-890 nm. The attenuation length (1/e attenuation) was calculated by assuming the validity of Beer's law: $I=I_0 e^{-A}$, where $I_0$ is the incident beam intensity and A is the film attenuation. The attenuation measurements were performed with baseline subtraction.

The attenuation length of the chitosan adhesive with and without IG (groups I and II) at 808 nm were respectively 5±1 µm and 228±72 µm. The presence of genipin in the adhesive (group III) did not change significantly the attenuation length (6±1 µm, n=3, p=0.38 t-test).

Figure 2:
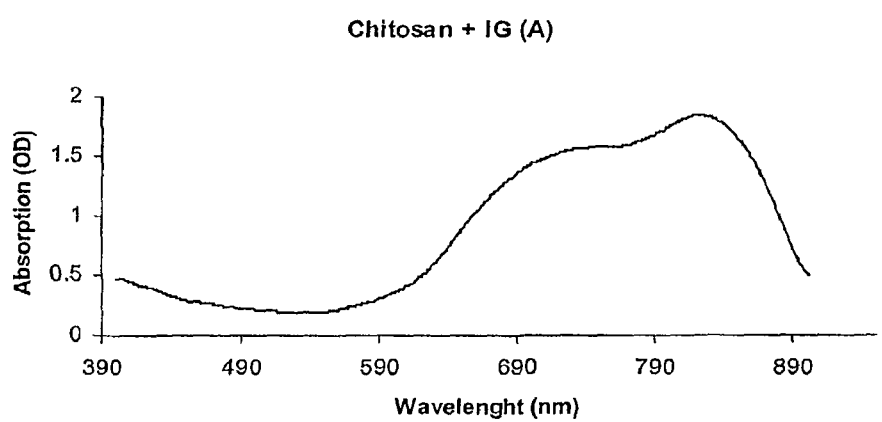
FIG. 2 shows a typical attenuation spectrum of a chitosan adhesive according to the present invention, in the visible-NIR region: a strong attenuation peak is localized at 808 nm, corresponding to the well-known absorption wavelength of IG dye (a), and another peak is located at 608 nm due, to the genipin crosslinked amino groups (b, c); no peaks are present in chitosan films without IG and Genipin (d)
Figure 2:
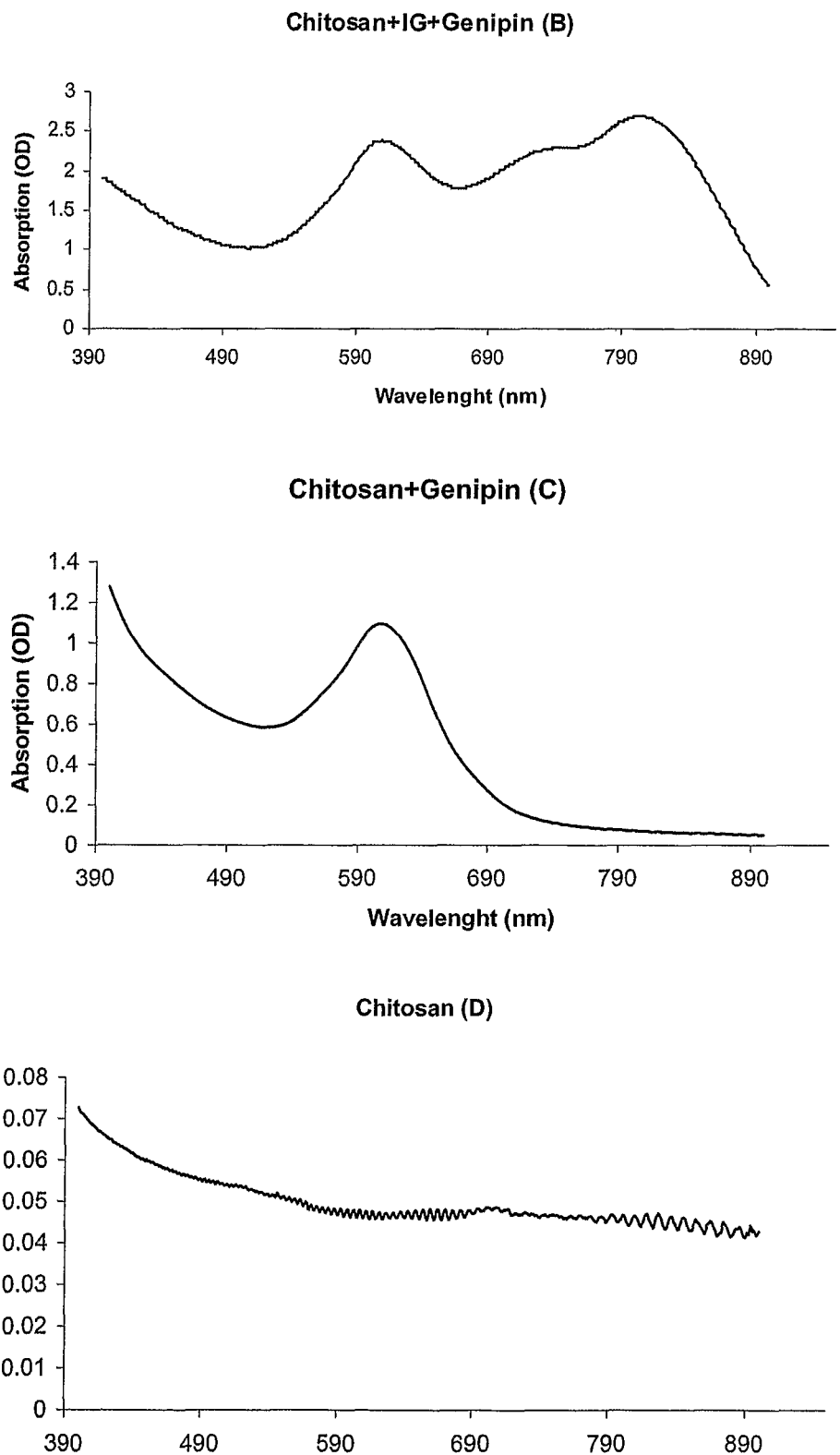

The attenuation length at 608 nm of the bluish chitosan adhesive with genipin (group IV) was 6±2 µm; the colour change of the chitosan strips and the peak absorption signalled crosslinking between genipin and chitosan amino groups. The presence of IG in the adhesive (group III) did not change significantly the attenuation length (7±1 µm, n=3, p=0.54 t-test). Assuming insignificant scattering and reflection, we may ascribe to IG the efficient absorption of the laser energy at 808 nm inside the chitosan adhesive, independently to the presence of genipin. In contrast, chitosan adhesive without IG was virtually transparent to the laser. The complete results are reported in table 1 and FIG. 2.

TABLE 1

Attenuation data of the adhesive at a wavelength of 808 and 608 nm; the mean value ± the standard deviation are given. N, number of adhesive samples analysed. Attenuation Length, 1/e attenuation of the chitosan adhesive, as calculated from Beer's law. Thickness, thickness of chitosan adhesives.

| Adhesive Type (N = 3) | λ (nm) | Thickness (µm) | Attenuation Length (µm) |
|---|---|---|---|
| Chitosan + IG (Group 1) | 808 | 30 ± 10 | 5 ± 1 |
|  | 608 | 30 ± 10 | 25 ± 6 |
| Chitosan (Group 2) | 808 | 30 ± 10 | 228 ± 72 |
|  | 608 | 30 ± 10 | 223 ± 68 |
| Chitosan + IG + Genipin (Group 1) | 808 | 40 ± 10 | 6 ± 1 |
|  | 608 | 40 ± 10 | 7 ± 1 |
| Chitosan + Genipin (Group 4) | 808 | 20 ± 10 | 129 ± 16 |
|  | 608 | 20 ± 10 | 6 ± 2 |

Example 3

Laser Tissue Repair (LTR)

Tissue repair was investigated by using a GaAlAs diode laser (Qphotonics, L.L.C., VA, USA), coupled with a multi-mode optical fiber through an FC connector. The fiberoptic cable was inserted in a hand-held probe to provide easy and precise beam delivery by the operator. The laser emitted at 808 nm, with a fiber core diameter of 200 µm, numerical aperture 0.22 and a beam spot size on the adhesive of approximately 1 mm. Because the laser is not eye safe (Class IV), safety goggles were worn by all staff in the operating theatre.

The diode laser was used to irradiate the chitosan-based adhesive strips to repair rectangular sections of sheep small intestine (~2×1 cm) under an operative microscope (×20). Fresh intestinal tissue was harvested from sheep immediately after euthanasia and stored at –80° C. Prior to use, tissue was immersed in deionized water for 15 minutes to defrost and hydrate at room temperature. The serosa layer of intestine consists of connective tissue that is rich in collagen and therefore suitable for testing the tensile strength of laser adhesive repairs. Intestine is abundant in the sheep body and a single animal can provide enough tissue for several trials.

Figure 3:
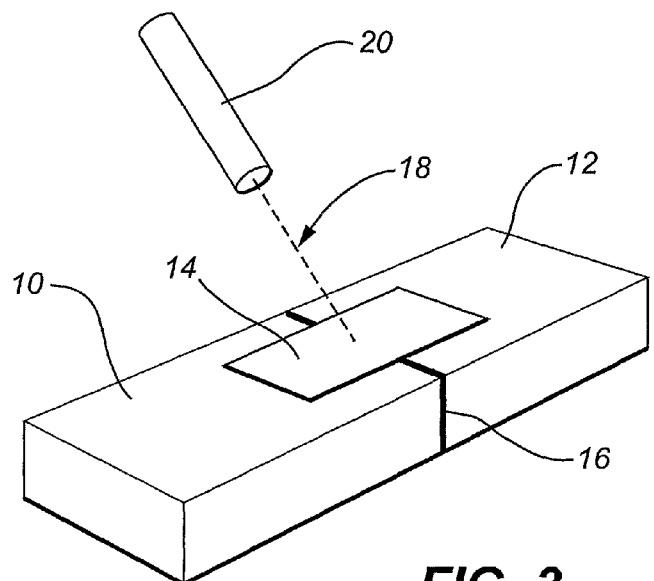
FIG. 3 shows a schematic top-view of laser tissue repairing, in which a strip of chitosan adhesive is applied across the incision and then subsequently irradiated using a laser.

Intestine sections were bisected by a full thickness incision with a #10 blade. The intestine was kept moist using deionized water; excess water was absorbed with sterile gauze or cotton tips prior to tissue repair. The process is illustrated in FIG. 3. The incision stumps 10 and 12 were approximated end-to-end and a chitosan strip 14 was positioned across the incision 16 on the serosa layer with microforceps ensuring full contact with the intestine. Thereupon, the operator irradiated the adhesive 14 by moving continuously the beam 18 (which was delivered from fibre 20) across its surface at a speed of ~1 mm/s and without charring or ablating the adhesive (FIG. 3).

A fluence of approximately 52 J/cm$^2$ was required to irradiate three times the adhesive strips at a speed of ~1 mm/s and power level of 120 mW. A similar fluence was also chosen for the other experimental groups. Moderate tissue shrinkage under the adhesive was observed during laser irradiation. Variable power and therefore irradiance was used in the first part of the experiment, to choose suitable parameters for tissue repair (table 2). In the second part of the experiment, the chitosan strips were tested using the selected power and irradiance (table 2). Control tissue repairs were also carried out, applying chitosan strips without the use of laser radiation.

TABLE 2

The laser parameters and adhesive characteristics (mean ± SD) are given for the repairing of sheep intestine. The chitosan strips had a thickness of 21 ± 2 μm.

| Power (W) | Area (mm$^2$) | Time (s) | Irradiance (W/cm$^2$) | Fluence (J/cm$^2$) | Shear Stress (KPa) |
|---|---|---|---|---|---|
| 0.16±0.01 | 22±2 | 75±11 | ~20 | 54±4 | 7.9±2.8 |
| 0.12±0.01 | 23±2 | 99±6 | ~15 | 53±1 | 13.2±3.9 |
| 0.08±0.01 | 22±2 | 140±11 | ~10 | 51±2 | 10.5±4.2 |
| 0 | 34±4 | 0 | 0 | 0 | 1.3±0.7 |

Legend.
Power, laser power during tissue repair;
Area, averaged adhesive surface area in contact to the intestine during laser repair;
Time, laser irradiation time;
Shear Stress, maximum load divided by the surface area of the chitosan adhesive.

Example 4

Tensiometer Measurements

The intestine was tested 10 minutes after tissue repair with calibrated tensiometer (Instron Mini 55, MA, USA) to assess the tensile strength of the repaired wound. Tissue was maintained in wet gauze after being repaired to mimic in vivo conditions and avoid sample desiccation. A specimen was clamped to the tensiometer using pneumatic grips, separating at a rate of 22 mm/min until the adhesive failed. The maximum load under which the adhesive failed was recorded by Merlin IX software.

Based on the tensiometer results, further physical, chemical and biological characterization of the strongest chitosan adhesive (among the four groups) was carried out as described in the following experiments.

TABLE 3

The laser parameters and adhesive characteristics (mean ± SD) are given for the repairing of rat intestine. The chitosan strips had a thickness of 20 ± 5 μm.

| Adhesive Group (N = 30) | Area (mm$^2$) | Power (W) | Time (s) | Fluence (J/cm$^2$) | Maximum Load (N) | Shear Stress (KPa) |
|---|---|---|---|---|---|---|
| Group 1 + Laser | 34±4 | 0.12±0.01 | 147±7 | 52±2 | 0.50±0.15 | 14.7±4.3 |
| Group 1 | 34±4 | 0 | 0 | 0 | 0.07±0.04 | 1.9±1.3 |
| Group 3 + Laser | 34±4 | 0.12±0.01 | 146±4 | 51±1 | 0.31±0.10 | 9.1±2.9 |
| Group 3 | 34±4 | 0 | 0 | 0 | 0.02±0.01 | 0.6±0.4 |

First Part

Figure 4A:
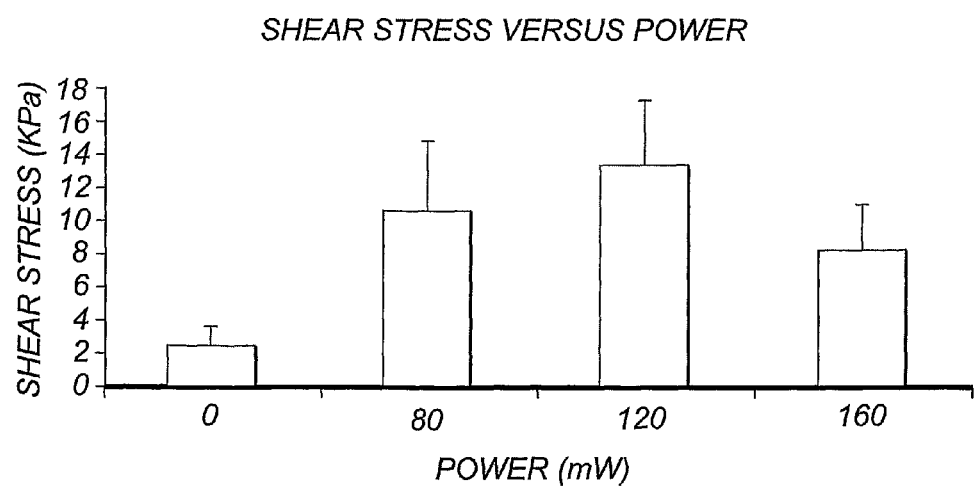
FIG. 4 shows a) a histogram of acute shear stress of chitosan adhesive (group I) versus laser power (mean ±SD); b) a histogram of acute shear stress of chitosan adhesives from groups I and III, with and without the aid of laser radiation (mean ±SD)

The chitosan strips failed at the tissue interface in all types of repair procedures (group I). The laser-irradiated strips fully bonded to tissue and adhered more firmly at 80 and 120 mW laser output (Anova one-way, p<0.001). Although there was no statistical difference between the shear stress of the adhesive irradiated at 80 mW and 120 mW (13.2±3.0 KPa and 10.5±4.2 KPa respectively, p>0.05 Bonferroni's post-test), it appeared that there was a trend for higher shear stress at 120 mW. The shear stress decreased to 8.0±2.8 KPa at 160 mW laser output; the chitosan strips sporadically burned and twisted during irradiation. The power level of 120 mW appeared the best choice for the second part of the experiment because of the high shear stress and because the surgeon irradiated the adhesive for a shorter interval. All results are displayed in FIG. 4a and table 2.

Second Part

Figure 4B:
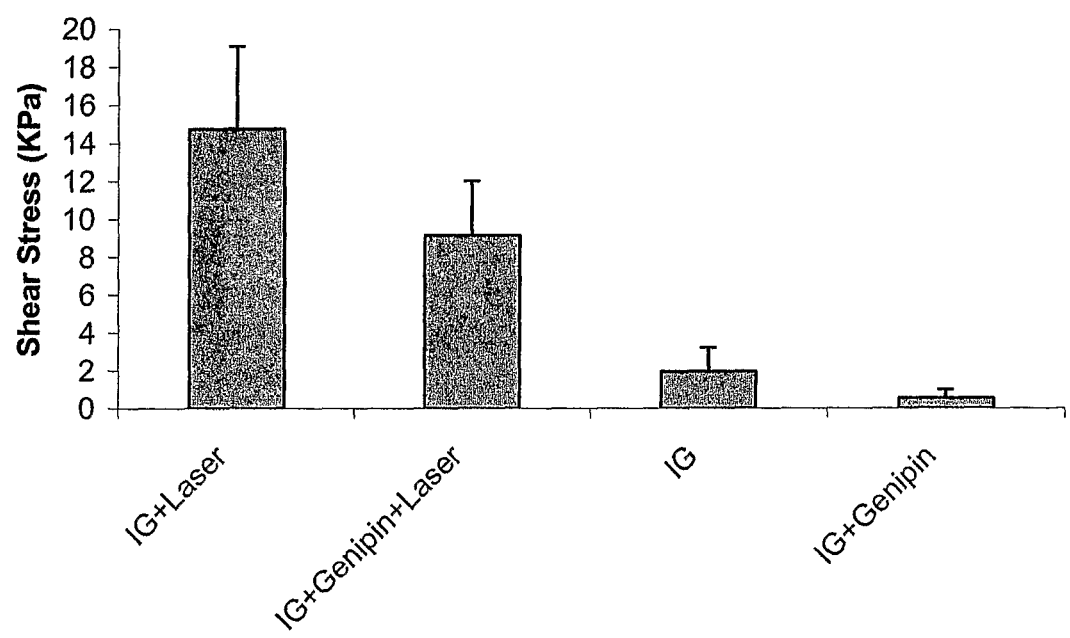

The adhesive with IG (group I) performed a stronger repair than the adhesive with IG+ Genipin (group III) after laser activation (14.7±4.3 KPa and 9.1±2.9 KPa respectively, n=30, p<0.001 t-test). Strips from the same groups resulted in a significantly lower intestine adhesion without the laser irradiation step (shear stress=1.9±1.3 KPa and 0.6±0.4 KPa, n=30, p<0.001, unpaired t-test). The strips failed at the tissue interface in all types of repair procedures but for the IG+ genipin adhesive (group III), that broke in two pieces in 30% of the repairs under the pulling maximum load. The chitosan strips from groups I and II were therefore selected for further characterization. All data are displayed in FIG. 4b and table 3.

Example 5

$^{13}$C-NMR

Solid-state $^{13}$C-NMR spectra were acquired using a Varian Inova-300 spectrometer operating at 75.45 MHz with Chemagnetics 7.5 mm double air-bearing cross-polarization (CP) probe. Samples of chitosan shells and white chitosan adhesive films (group II) (~200 mg) were packed as strips and pieces into 7.5 mm od rotors made from partially-stabilized zirconia and subjected to "magic-angle spinning" at 2-3 kHz. IG dye was not included in the analysed adhesive to avoid possible signal interference in the spectrum. Spectra were acquired at 294 K using single-contact cross-polarization experiments with high-power $^1$H decoupling during acquisition. The following parameters were found optimal: pulse width 5.2 μs (90°); contact time, 1 ms; recycle time, 5 s. Free induction decays were acquired and zero-filled to 8 K prior to Fourier Transformation. Up to 10,000 scans were collected for sufficient signal/noise. The Hartman-Hahn match was set using hexamethylbenzene, which was also used as a secondary external reference that gives the methyl peak, $\delta_c$=17.3 ppm on the tetramethylsilane scale ($^{13}$C TMS=0 ppm).

Figure 5A:
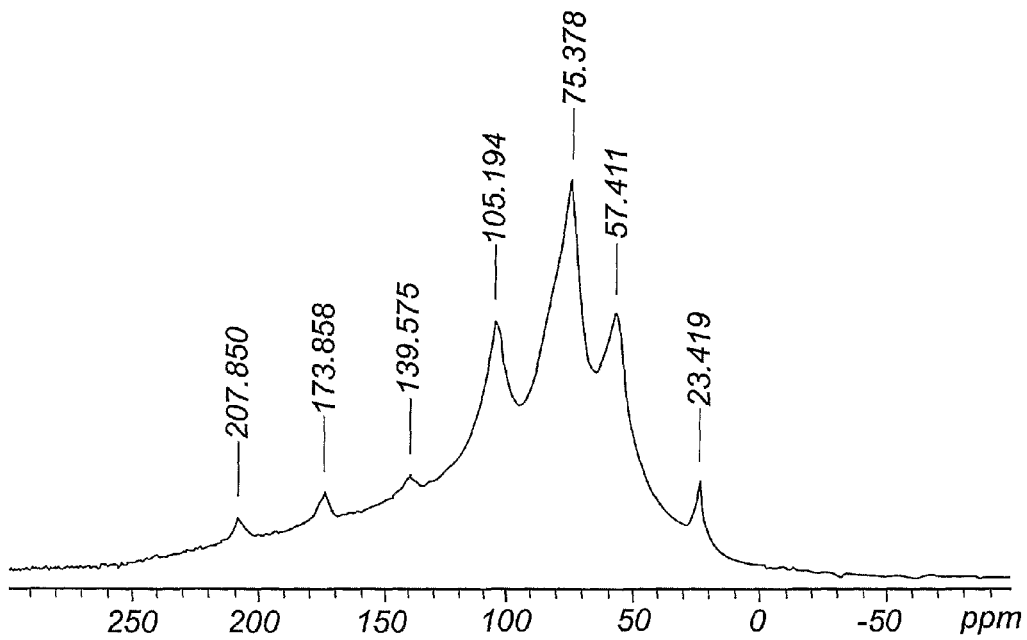
FIG. 5 shows $^{13}$C-NMR spectra of chitosan shells (a) and adhesive (b), illustrating that the glucosamine moiety at ~104 (C1), 77 (C3-5), 57 (C2, C6) ppm, is present in chitosan shells and adhesive; the residual acetate group from the unhydrolysed chitin, at ~174 (C=O) and 24 (CH$_3$) ppm are augmented in the adhesive spectrum by acetic acid; no significant chemical changes occurred during the preparation of the chitosan adhesive.
Figure 5B:
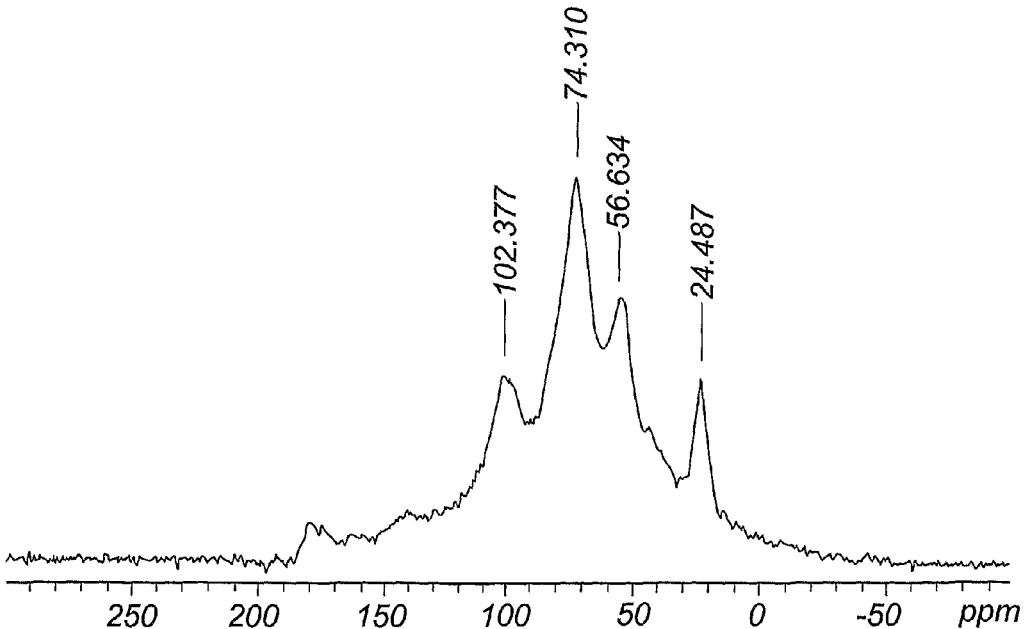

The solid-state $^{13}$C-NMR spectra of commercially available chitosan, and the chitosan adhesive (group II) are displayed in FIGS. 5a and 5b respectively. No significant chemical change occurred during the preparation of chitosan adhesive. In both spectra there are the peaks expected for the glucosamine moiety at ~104 (C1), 77 (C3-5), 57 (C2, C6) ppm. In the commercial chitosan sample the peaks for the residual acetate group from the unhydrolysed chitin at ~174 (C=O) and 24 (CH$_3$) ppm could be readily observed, while in that for the chitosan adhesive, the acetate peaks are augmented by the acetic acid used in the preparation of the adhesive. The peaks are relatively broad reflecting the amorphous nature of these materials.

Example 6

Thermogravimetric Analysis (TGA)

Chitosan adhesive films were analysed using a Perkin Elmer Pyris 1 Thermogravimetric.

Figure 6:
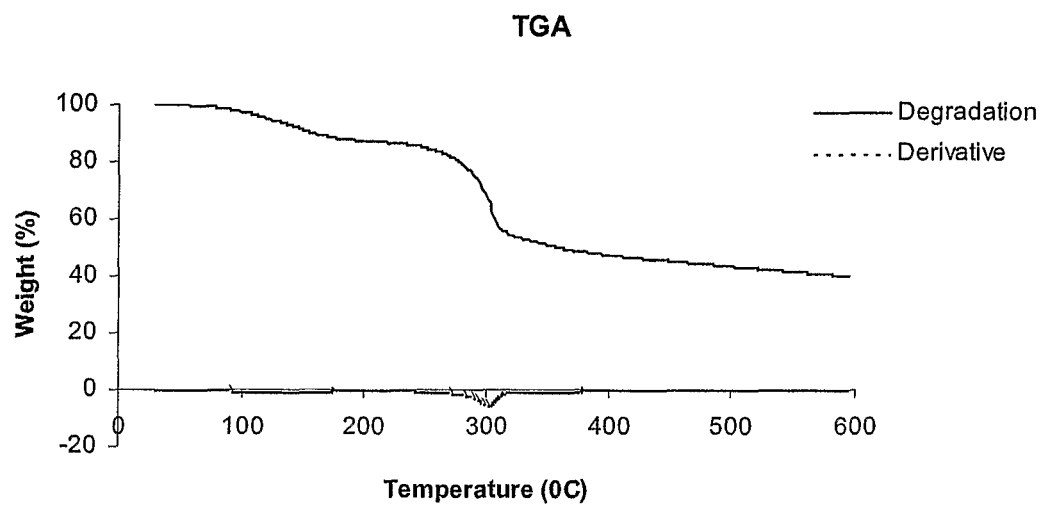
FIG. 6 shows the weight loss of a chitosan adhesive according to the present invention as a function of temperature, wherein water evaporated up to 211° C., reducing the adhesive weight of 13% (first derivate=0) and the adhesive burnt at ~317° C., where the weight loss rate achieved its maximum (minimum peak of the first derivative)

Analyser to evaluate the water content and degradation temperature of the films in air (weight 10-15 mg). The temperature was increased from 20 to 600° C. at a rate of 40° C./min. The mass of the films was continuously recorded as a function of temperature and the first derivative calculated to assess the adhesive degradation (derivative minimum peak) and water content (derivative=0). The TGA analysis of the adhesive with IG (group I) showed an initial sample weight loss of 11.9±0.6% (n=6) at 202±15° C. (FIG. 6). It is most likely that during this phase water evaporated. The adhesive degraded further and its weight diminished to 34.5±3.6% at 304±2° C., the temperature of maximum rate of weight loss (derivative minimum peak). Similar results were achieved by the adhesive without IG (group II). The adhesive water content and the mass loss were not statistically different respect to the group I adhesive (13.2±0.6% and 37.4±1.5% respectively, n=5, p>0.05 student's t-test), though the degradation temperature was higher (317±2° C., p<0.001 student's t-test).

Example 7

Differential Scanning Calorimetry (DSC)

Thermograms of chitosan adhesives were obtained and recorded by using a differential scanning calorimeter (DSC 7, Perkin-Elmer, USA). The samples (10-15 mg) were accurately weighed into solid aluminum pans and sealed. Heating rates of 10° C./min, 30° C./min and temperature ranges of 20-110° C. (n=14) or 25-220° C. (n=4) were selected for scanning under air with a flow rate of 20 mL/min. The scans were repeated twice at a cooling rate of 30° C./min to thermally stabilize the system and eliminate possible thermogram artifacts. The temperature range was not extended further to avoid heavy degradation of samples and allow the detection of a possible melting transition. The software Pyris analyzed data and calculated the temperature of transitions points.

Figure 7:
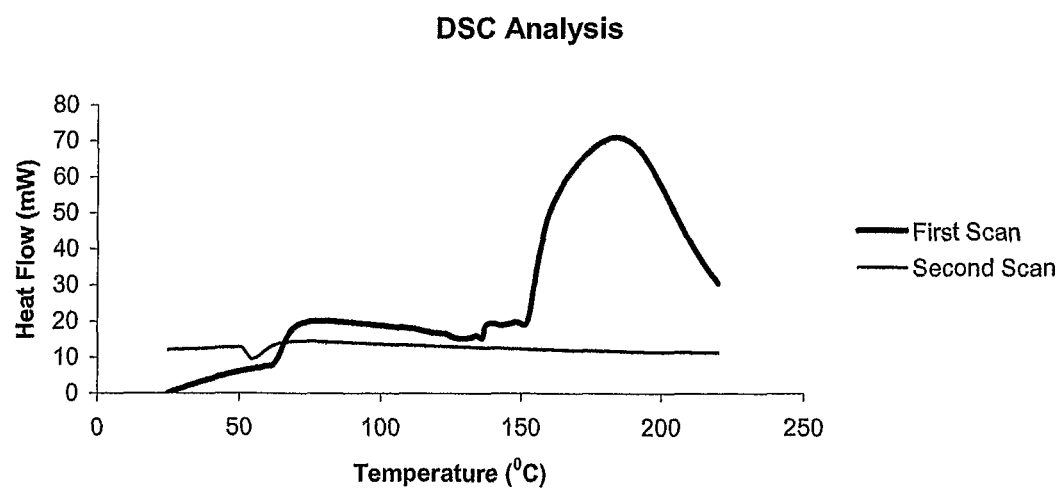
FIG. 7 shows DSC scans of chitosan adhesives according to the present invention, which display a broad degradation peak between 150 and 200° C. that disappears in the second scan: no other transition occurred below 150° C.

The thermograms of the adhesive (group I) showed a broad peak of heat absorption between 150 and 220° C. that disappeared during the second scan (FIG. 7). Chitosan degradation therefore occurred rather than melting at these temperatures, in agreement with the TGA study. If the adhesive melted, a similar peak should have also appeared in the second scan. No other transition was observed below 150° C.

Example 8

Contact Angle

The static contact angle of chitosan adhesives was measured by the sessile drop method using the RHI system (model 100-00-230, New Jersey, USA). The films were positioned on a translating stage and a drop of water poured on them. A CCD camera recorded the image of the drop on films provided by a telescope with magnification of 23; the system software measured the contact angles. Six readings from different parts of the film surface were averaged to give the mean contact angle.

Figure 8:
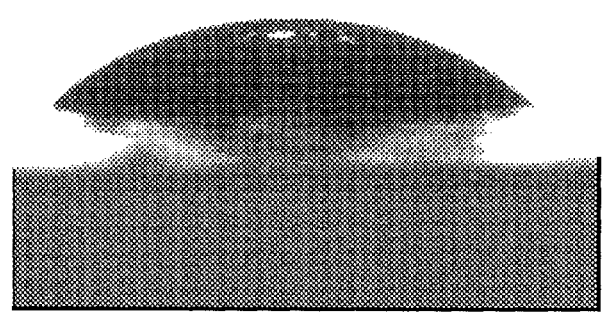
FIG. 8 illustrates measurement of contact angle of a water drop on chitosan adhesive according to the present invention.

The contact angle of the adhesive was 47±4 degrees (n=6), consistent with a moderately hydrophilic nature (FIG. 8).

Example 9

Atomic Force Microscopy (AFM)

The surface topography of chitosan adhesives was imaged by using a commercial atomic force microscopy (Digital Instruments Dimension 3000, Urbana, Ill., US). The microscope was operated in tapping mode using silicon cantilevers with a nominal spring constant of 40 N/m and oscillating with average amplitude of 100 nm and a resonance frequency between 200 and 450 kHz. The scanning rate was automatically selected. Surface roughness was calculated as the Z RMS value:

$$Rq = [\Sigma_i (Z_i - Z_{ave})^2/N]^{1/2}$$

where $Z_{ave}$ is the average Z value within the scanned area, $Z_i$ is the current Z value and N is the number of points in the scanned area.

Nine measurements of this surface parameter were performed on three separate films; Rq mean and standard deviation were also calculated.

Figure 9A:
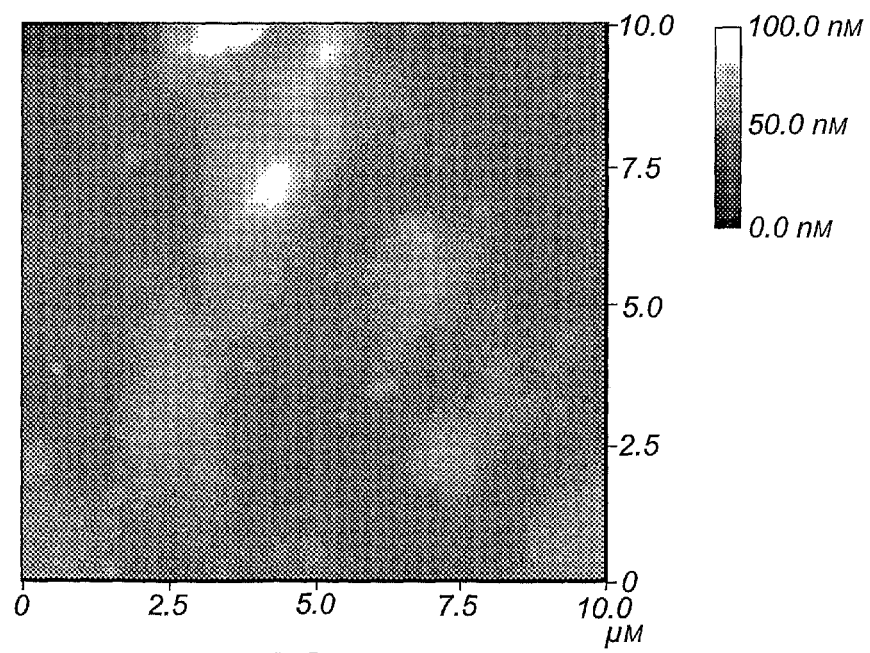
FIG. 9 shows AFM images of the chitosan adhesive according to the present invention: a) topography of the chitosan adhesive obtained with AFM, showing how irregular peaks appeared sporadically throughout the film surface; b) three dimensional view of the adhesive surface.
Figure 9B:
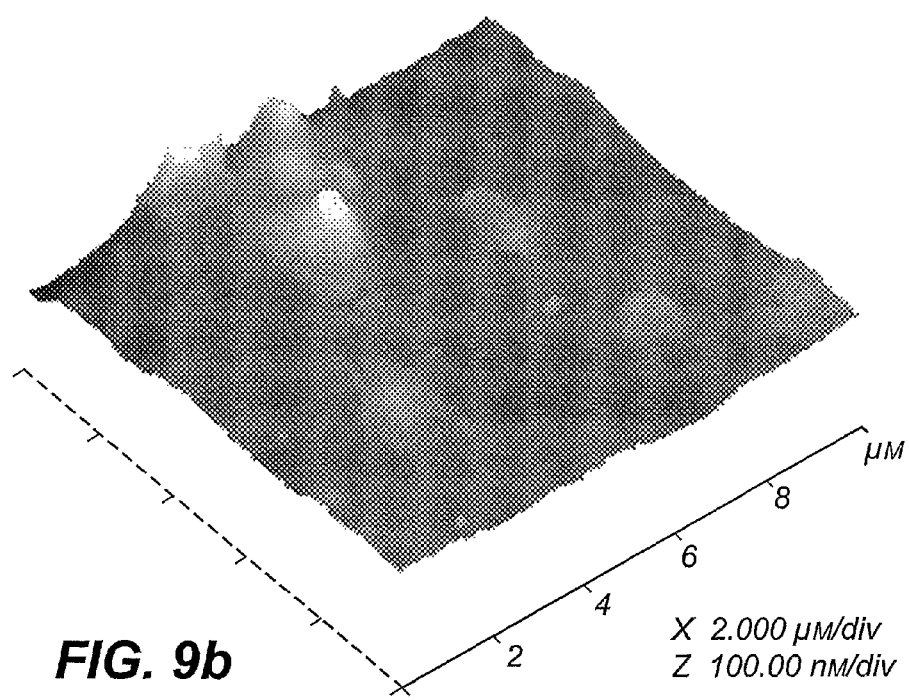

The profile of the film surface was relatively smooth (Rq=6.7±4.0 nm, n=9) as irregular corrugations appeared sporadically over the chitosan film. The surface topography is shown in FIG. 9.

Example 10

Young's Modulus

Rectangular strips of chitosan adhesives from groups I and II were also tested alone by the tensiometer to measure their Young's modulus (E) without laser activation. The strips (N=15) were wet with water and fixed to the grips, which moved apart until the repair failed. The software generated a strain-stress plot and calculated, E in the strain region between 10% and 20%, assuming the strip thickness remained constant throughout elongation.

Figure 10:
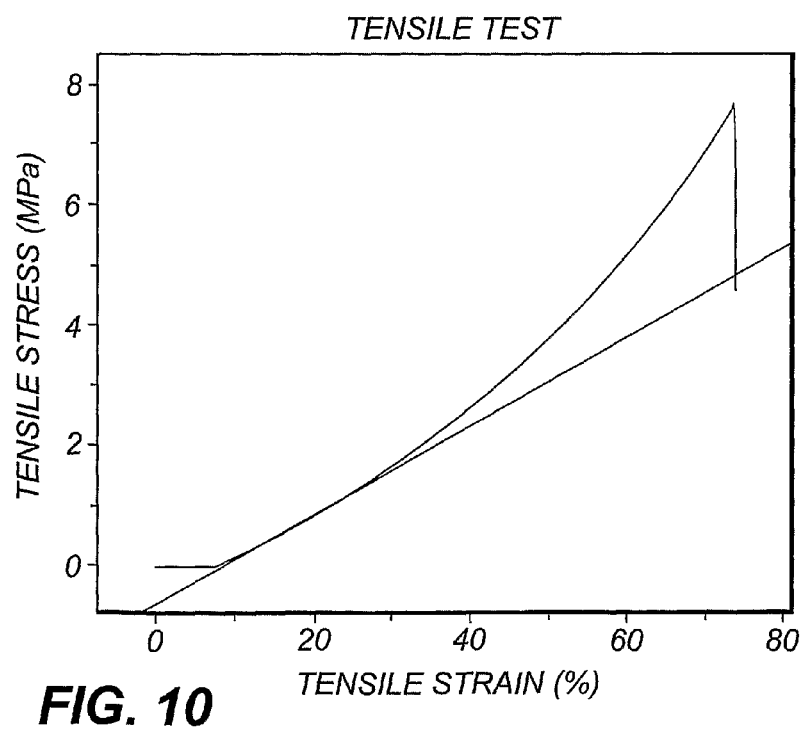
FIG. 10 is a graph illustrating the stress and strain relationship for wet chitosan adhesive according to the present invention: the E modulus (~7.3 MPa) was calculated in the strain region between 10 and 20%, where the adhesive shows its elastic behaviour.

Young's modulus of wet chitosan strips from groups I and II were respectively 7.85±1.5 MPa and 6.81±1.26 MPa (n=15, p>0.05 student's t-test). The presence of IG appeared not to alter significantly the elastic modulus of the adhesive. When combined, the above results yield to E=7.3±1.5 MPa (n=30). The adhesive not only showed high tensile strength but also flexibility as it could be flexed to ~160 degrees without suffering macroscopic damage. The tensile test results are summarized in FIG. 10.

Example 11

Temperature Measurements

Figure 11:
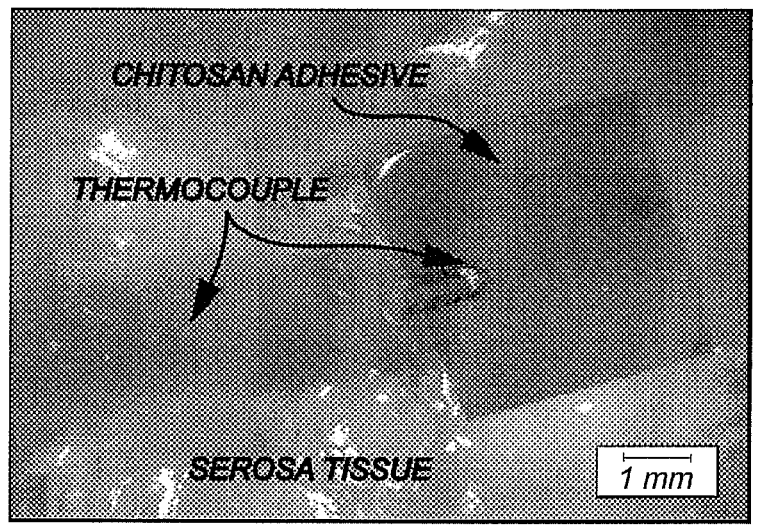
FIG. 11 is a photograph showing a strip of chitosan adhesive according to the present invention bonded to the serosa layer of intestine: a thermocouple was placed between tissue and adhesive to record the temperature during LTR.

The temperature of LTR (laser tissue repair) was measured with an insulated K-type thermocouple (diameter=0.25 mm, response time=0.1 s) positioned between the intestine and adhesive as illustrated in FIG. 11.

The thermocouple was connected to a signal-conditioning unit (SCXI-1121) with 4 Hz low pass analogue filter. Data were sampled at 10 Hz with a 12-bit data acquisition board (PCI-6024E) controlled by LabView® (National Instruments, Austin, Tex., U.S.) The strips were irradiated, as described previously, by moving continuously the beam across the adhesive surface; temperature data were recorded for 20 s while the beam was directed on the thermocouple or in its proximity. After LTR, the adhesive was detached using microforceps to ensure that tissue adhesion occurred.

Figure 12:
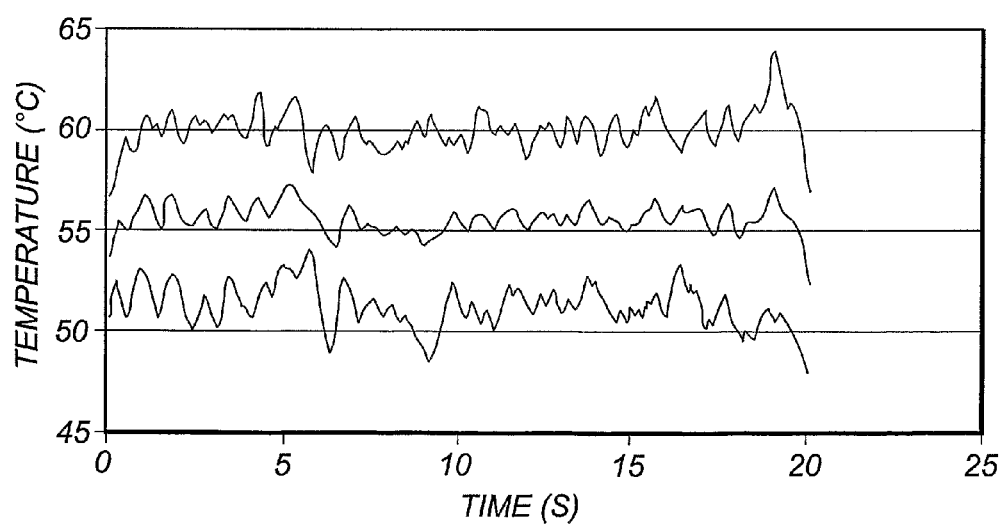
FIG. 12 is a graph illustrating the temperature of the thermocouple, under the chitosan adhesive at tissue interface, as a function of time: the mean temperature ±standard deviation (n=15) is also provided to indicate the temperature range during LTR.

The average temperature for LTR with chitosan adhesive (group I, n=15) was 57° C. (FIG. 12). The laser output raised sporadically the temperature to a maximum level of ~65° C. and this always resulted in charring of the adhesive. Moderate tissue shrinkage under the adhesive was observed whenever the thermocouple measured temperatures above 60° C. The efficient absorption of IG prevented IR radiation to directly affect the thermocouple and alter the temperature measures.

The irregular profile of the temperature plots in FIG. 12 is a reflection of the free hand use of the laser and is typical of surgical procedures.

Example 12

Ex-Vivo Histology and Scanning Electron Microscopy (SEM)

Intestine was harvested immediately after sacrificing sheep and stored in phosphate buffer solution at 4° C. for half an hour. Tissue sections (n=4) were thereupon repaired as explained previously using the same parameters listed in table 2. They were stored in 10% buffered formalin and fixed for Hematoxylin and Eosin (H&E) staining.

The purpose of this study was to show acute thermal damage such as ablation, charring or coagulation.

Other repaired tissue was prepared for SEM analysis (n=4). Chitosan repaired intestine was cut with a scalpel to small pieces (~1×2 mm) and fixed in Karnovsky's solution (2.5% paraformaldehyde and 2% glutaraldehyde in 0.1 M phosphate buffer) after being gently washed in 0.1 M phosphate buffer and dehydrated in alcohol at several dilutions (30%, 50% and 70% v/v). Specimens were further dehydrated to critical point and sputter coated with Cu before being viewed at 10 KV by the microscope in high vacuum mode (FEI Quanta 200, Hillsboro, Oreg., US).

Figure 13A:
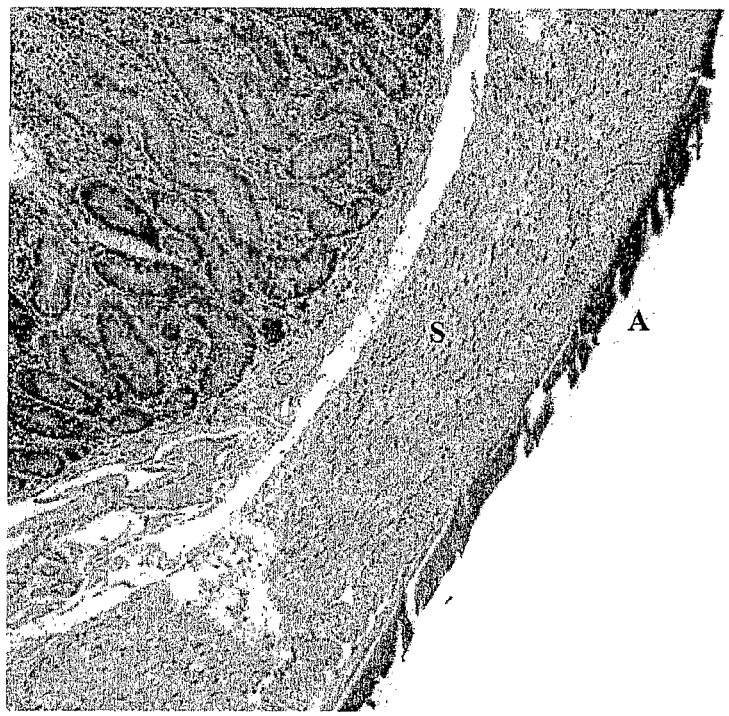
FIG. 13 shows micrographs of the adhesive: a) longitudinal section of the adhesive (A) laser-bonded to the intestine serosa (S) (H&E, ×10); b) the serosa suffered mild thermal damage (D) soon after irradiation if compared to the control: cell nuclei are stained blue (N) (H&E, ×20); c) non laser irradiated intestine: the serosa appears healthy (H&E, ×10)
Figure 13B:
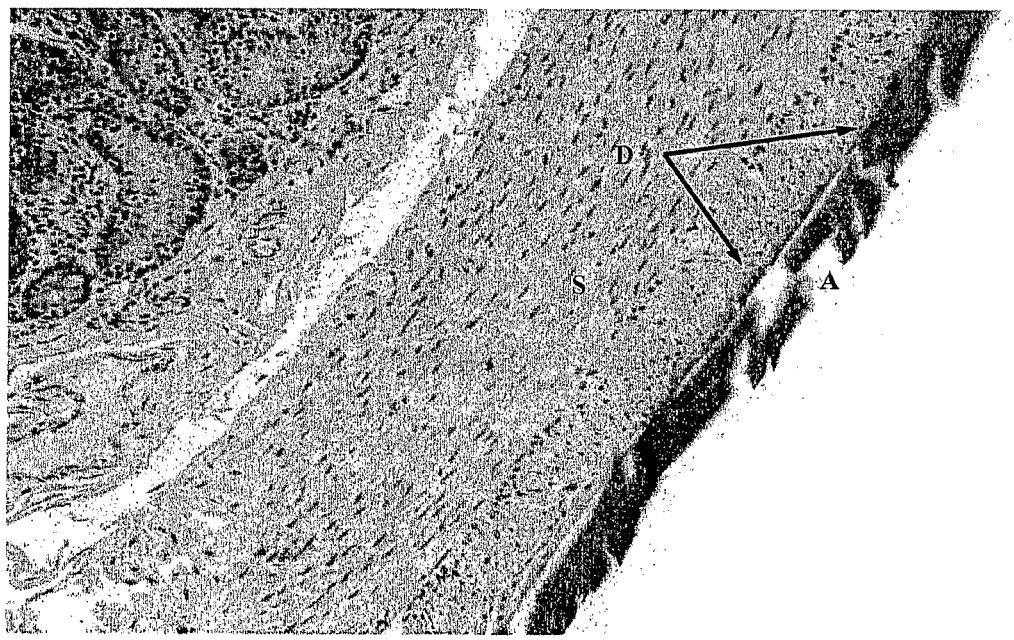
Figure 13C:
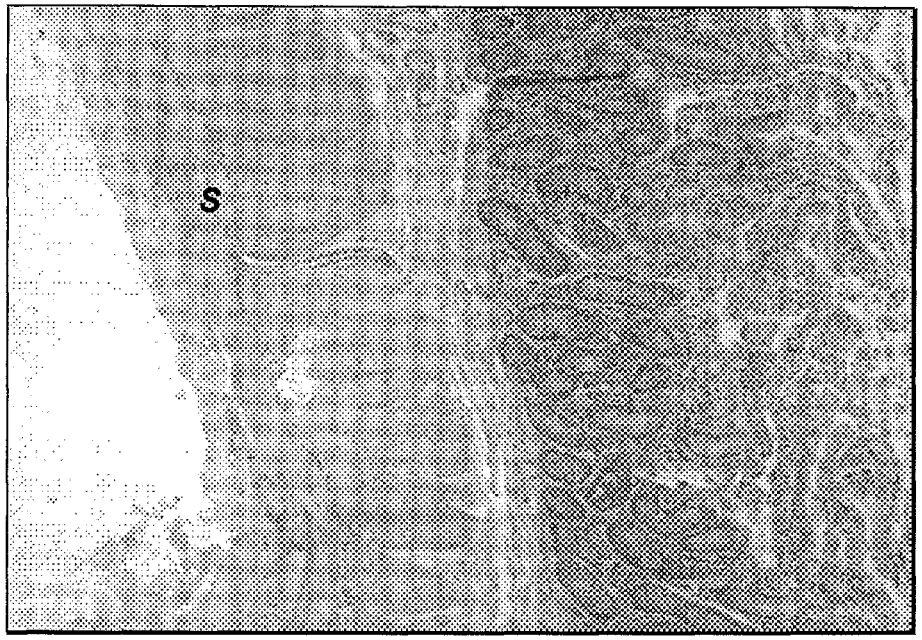

Although the laser heat caused tissue coagulation in the proximity of the chitosan adhesive (~20 μm), no signs of tissue ablation, charring or vacuoles were observed in the histological sections (FIG. 13).

Figure 14A:
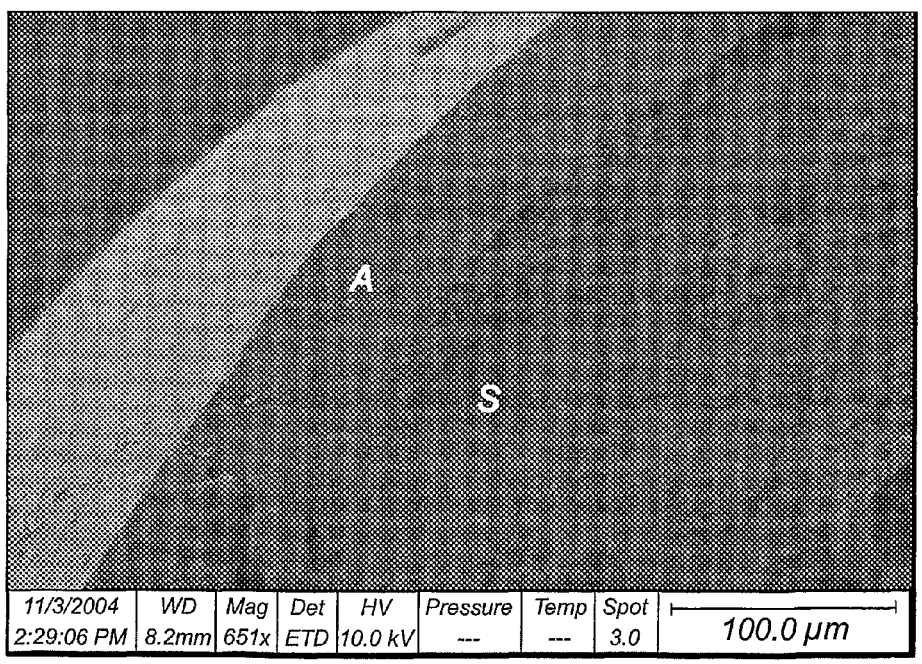
FIG. 14 shows SEM images: a) cross section of a chitosan strip according to the present invention (A) bonded on sheep intestine (S); b) cross section of a chitosan strip (A) bonded on sheep intestine (S) at higher magnification; c) collagen fibers (F) stretched and clearly bonded on the adhesive (A)
Figure 14B:
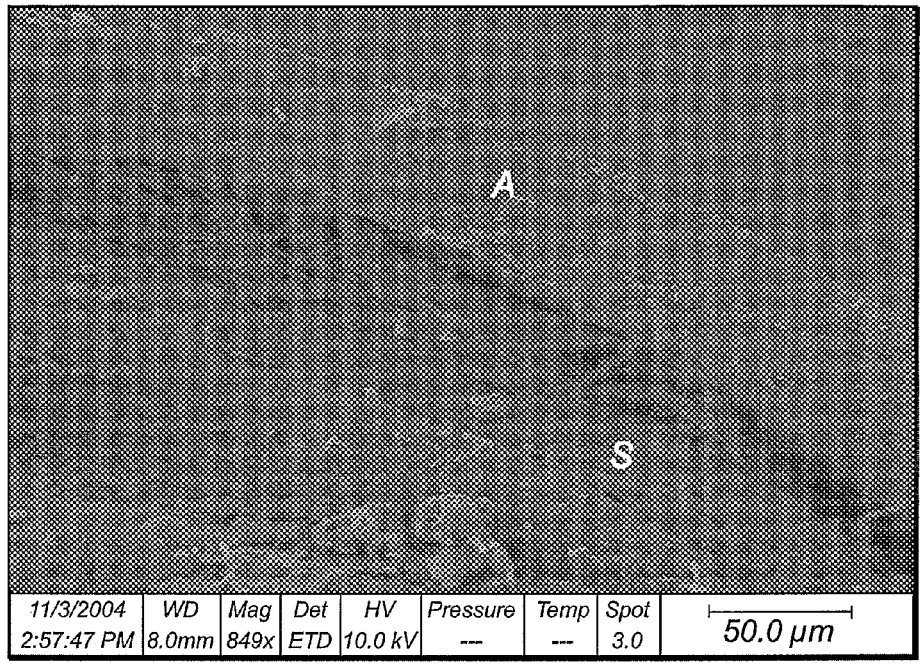
Figure 14C:
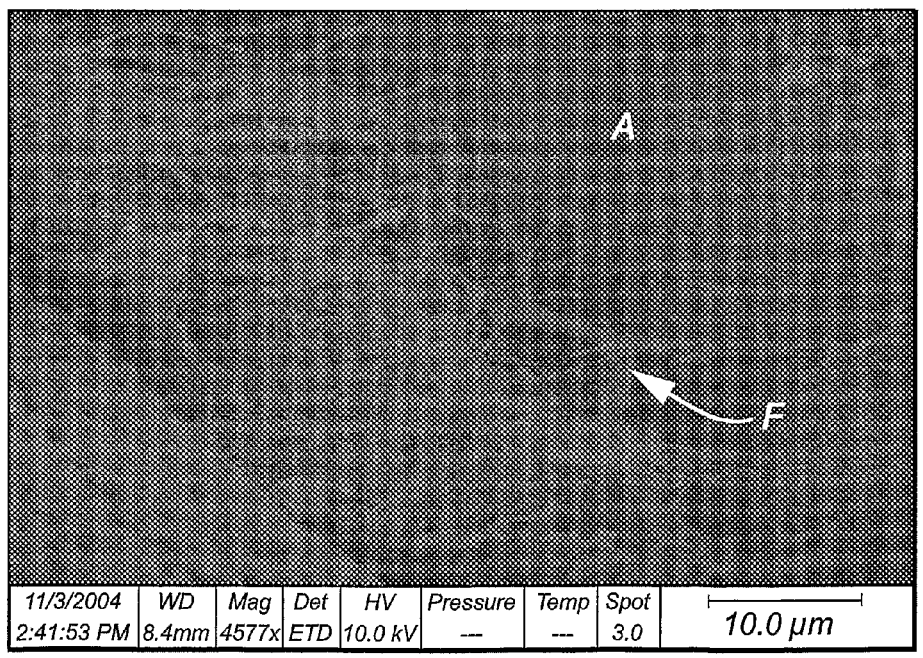

SEM images confirmed the intestine serosa bonded to chitosan strips, even if the adhesion line was sporadically interrupted. Artefacts during tissue manipulation may have caused such detachment (FIG. 14).

Example 13

Cytotoxic Assay

A cell growth inhibition assay was used to assess the cytotoxic potential of the chitosan adhesive films. Inhibition of cell growth in contact with extracts from these samples was compared with untreated medium and positive controls containing 7.5% ethanol. Murine L929 cells (Earle's L Cells—NCTC Clone 929) were established at ~$10^5$ cells per 35 mm diameter petri dishes. Cells were incubated at 37° C. for 24 hours in a 5% $CO_2$ humidified atmosphere using Earle's minimum essential medium (EMEM) supplemented with 10% Foetal Bovine Serum. After 24 hours, a sub-confluent cell monolayer was established and the medium was aspirated from the petri dishes. The medium was replaced with either a medium extract of the chitosan adhesives (group II) or with the controls.

All solder samples were γ-radiated in sealed Sterifilm® at a level of ~2.4 KGy to ensure sterile conditions (0.1 KGy/h for 24 hours). Chitosan films without IG (group II) and with surface area of ~18 $cm^2$ were placed in 3 ml medium (EMEM) in glass vials for 24 h at 37° C. The extract was removed and placed directly on the cell monolayer for 48 hours, as prescribed by the international standards (ISO/DIS 10993-12.2, 1996). During this time any cytotoxic components emanating from the test materials would have disrupted the growth of cells in the culture dish. At the end of the test period, cells were harvested, their numbers assessed through Flow Cytometry (FACS, Becton Dickinson, USA) and compared with untreated cultures (blank and null samples). No IG was added to the chitosan strips to avoid possible interference with the fluorescence signal of the assay. Assessment via Flow Cytometry was facilitated by the addition of Propidium Iodide (10 μg/ml), which stains non-viable cells with a disrupted membrane. Cells were harvested into a known volume and a known number of ~10 μm diameter polystyrene beads was added to the cell suspension. The number of cells in suspension was back calculated by comparing the ratio of cells to beads acquired by flow cytometry. Viability staining, forward scatter and side scatter evaluation by Flow Cytometry provided a more sensitive indication of material toxicity than inhibition alone.

Figure 15:
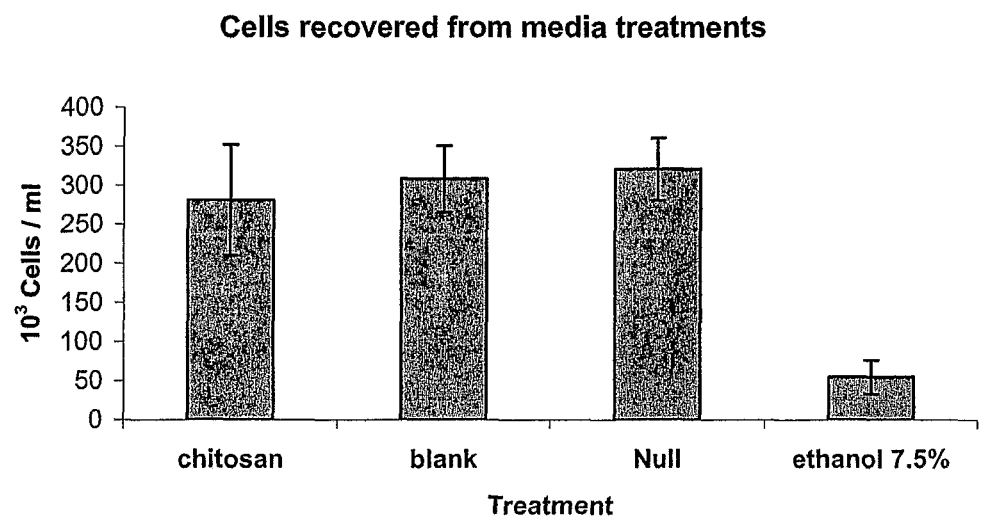
FIG. 15 is a histogram illustrating the number of cells recovered as a function of media treatment (mean ±standard deviation): the chitosan adhesive extracts were not cytotoxic to fibroblasts when compared to the null and blank, and solutions 7.5% ethanol significantly inhibited cell growth (positive controls); [Legend: Ethanol, samples of cells exposed to media with ethanol at 7.5% concentrations (v/v); Null, sample of cells exposed to fresh media; Blank, sample of cells exposed to media, which was incubated for 24 hours in 5% CO$_2$ air at 37° C.; Chitosan Adhesive, samples of cells exposed to media, which was incubated with chitosan adhesive for 24 hours in 5% CO$_2$ air at 37° C.]
Figure 16:
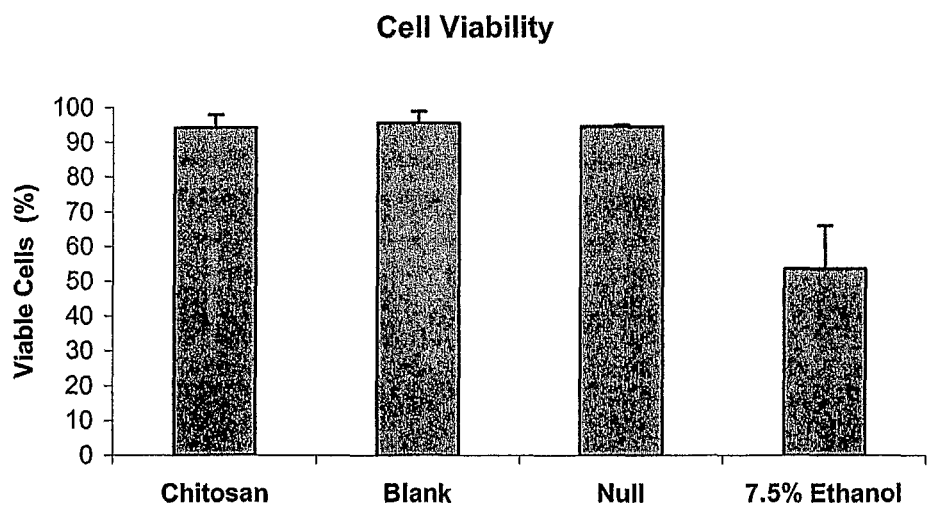
Figure 17:
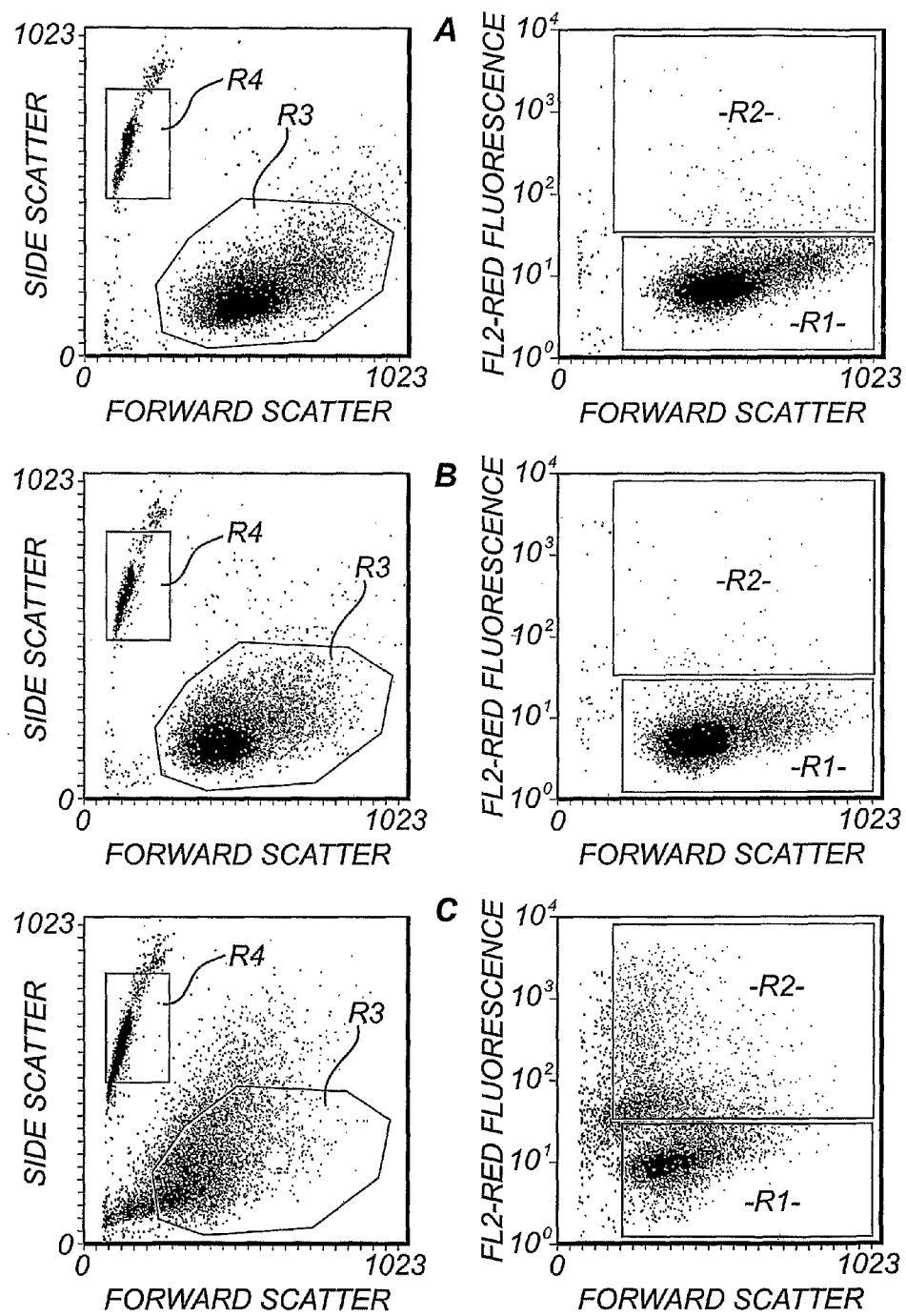
FIG. 17 shows flow cytometer plots of cell fluorescence and forward/side scatter: cells with their membrane broken fluorescence red light and are visualized in the R2 region while healthy cells are located in the R1 region, and cells extracted from chitosan (a) and untreated media (b) are healthy but many cells have their membrane broken after ethanol incubation (c)

The chitosan adhesive appeared to induce negligible cytotoxicity (FIG. 15). One-way variance analysis indicated a significant difference between the controls and experimental groups ($p<0.0001$). In particular, there was no statistical difference between the cell number of the null (n=3), blank (n=6) and chitosan extracted samples (n=9, cell number $>280*10^3$, $p>0.05$, Bonferroni's post-test). The growth of cells treated with ethanol (n=3) was significantly inhibited when compared to the growth of the chitosan extracted samples and negative controls (cell number $<55*10^3$, $p<0.001$, Bonferroni's post-test). Viability of the cells cultured in the chitosan extract, null and blank were greater than 95%, while cells cultured in the 7.5% ethanol control had a viability of 53% (FIG. 16). Forward and side scatter provided a qualitative evaluation of cell health; cells cultured in chitosan extract appeared equivalent to cells harvested from the blank or null (FIG. 17). The addition of 7.5% ethanol to culture media resulted in a qualitative changes to the cell shape, which was easily observed in their forward and side scatter. This detailed evaluation allowed for detection of toxic properties at doses lower than what would be statistically detectable in growth inhibition and confirmed the non cytotoxic properties of the chitosan adhesive.

Example 14

In Vivo Thermal Damage

The thermal damage induced by the laser activation of chitosan adhesive was assessed in vivo by irradiating chitosan strips on rat sciatic nerves. This animal model proved in previous studies to be a reliable test for the safety and efficacy of laser-activated albumin solders, as myelinated axons of peripheral nerves are sensitive to thermal damage. Six adult male Wistar rats, weighing approximately 600 g, were used in this preliminary study.

Figure 18:
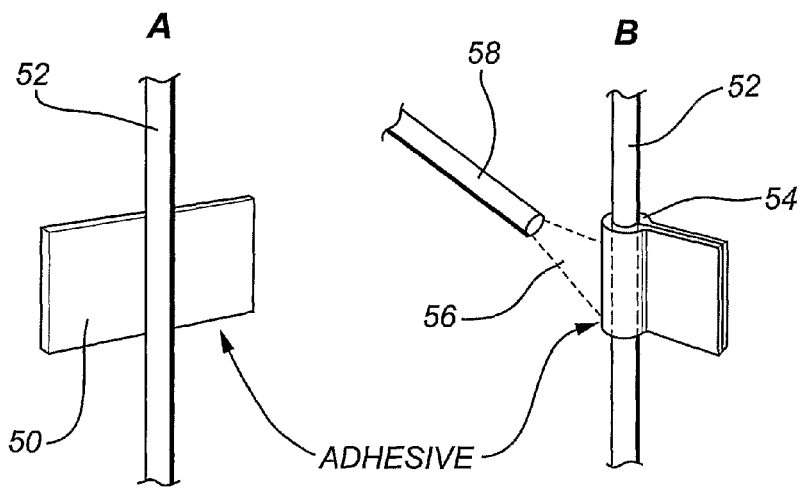
FIG. 18 illustrates the process of repairing a nerve using the present invention: the adhesive is firstly placed underneath the sciatic nerve (a), and then the chitosan strip adheres to the nerve like a collar before the laser irradiation takes place (b)

Anaesthesia was induced and maintained during surgery with Halothane/$O_2$ mix (4% during induction, 2% thereafter) using a standard anaesthetic machine. The surgical operation was performed using a Zeiss OPMI 7 operating microscope, and the operative procedure was performed under sterile conditions. An oblique skin incision of about 3 cm was made in the dorso-lateral part of the right thigh. The muscles were gently retracted and the sciatic nerves (dimeter ~1 mm) exposed at the sciatic notch. The adventitia of the sciatic nerve was partially peeled and trimmed with straight microscissors before applying the adhesive; excess water was absorbed with sterile gauze or cotton tips. As shown in FIG. 18, chitosan strip (group I) 50 with a thickness of ~20 μm and surface dimensions of ~6×5 mm was then positioned underneath the sciatic nerve 52 using microforceps. The chitosan strip 50 adhered fully to the nerve 52 like a collar (54) and assisted with rotation of the nerve, during the procedure (FIG. 18). The laser beam 56 from laser 58 was passed over the length of the strip three times to activate its adhesion to the epineurium, as described in the LTR example. The output power, fluence and beam spot size were 0.12±0.01 W, 65±11 J/cm², and ~1 mm respectively. During laser irradiation, the nerve perineurium was observed to shrink moderately. Rotation of the nerve 52 was obtained by gently moving the chitosan collar 54, so that the chitosan strip could be irradiated around the nerve (FIG. 18). The redundant chitosan was trimmed from the collar before closing the muscles and the skin with five 3-0 sutures. The animals were thereupon placed in individual cages with no restriction of movement.

Sections of the operated nerves were harvested at the operated sites, proximally and distally, four days after surgery. They were stored in 10% buffered formalin and fixed with Luxol Fast Blue and H&E staining to assess myelinated axons and tissue thermal damage. Sciatic nerves were also harvested from the left thigh to serve as controls. At the end of the procedure the animals were sacrificed by an intracardiac injection of 2 ml Sodium Pentobarbital.

Three sections (~2 cm) of sciatic nerves were also used for laser repair and measurement of shear stress. Each nerve section was cut in two equal parts by a microscissor, a chitosan strip was then positioned underneath the severed nerve and the stumps aligned end-to-end with micro-forceps. The chitosan strip adhered fully to the severed nerve like a collar and assisted with rotation of the nerve during the laser repair, as detailed above. The output power, fluence and beam spot size were 0.12±0.01 W, 46±2 J/cm² and ~1 mm respectively. The shear stress of the adhesive bonded to the nerve was tested by the Instron tensiometer as described before.

Figure 19A:
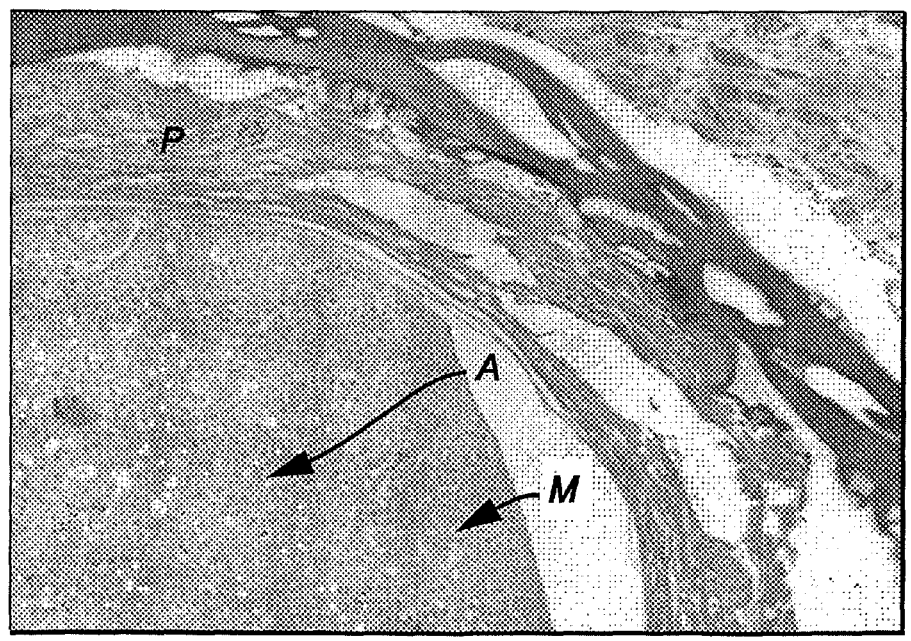
FIG. 19 shows micrographs of operated nerves: a) cross section of an operated nerve, showing where the adhesive (C) was laser-bonded to the perineurium (P); several axons are demyelinated (A) while others preserve the blue myelin sheet (M) four days post-operatively (Luxol Fast Blue, ×20); b) particular of FIG. 19a at higher magnification ((Luxol Fast Blue, ×40); c) cross section of the laser operated nerve at the distal site, illustrating how several axons preserve their myelinated sheet (M) while others are demyelinated (A) (Luxol Fast Blue, ×20); d) cross section of the proximal site of the laser operated nerve, illustrating that the majority of axons retained their normal morphology (Luxol Fast Blue, ×20); e) Cross section of a non operated sciatic nerve, illustrating that the majority of axons are myelinated (Luxol Fast Blue, ×20)
Figure 19B:
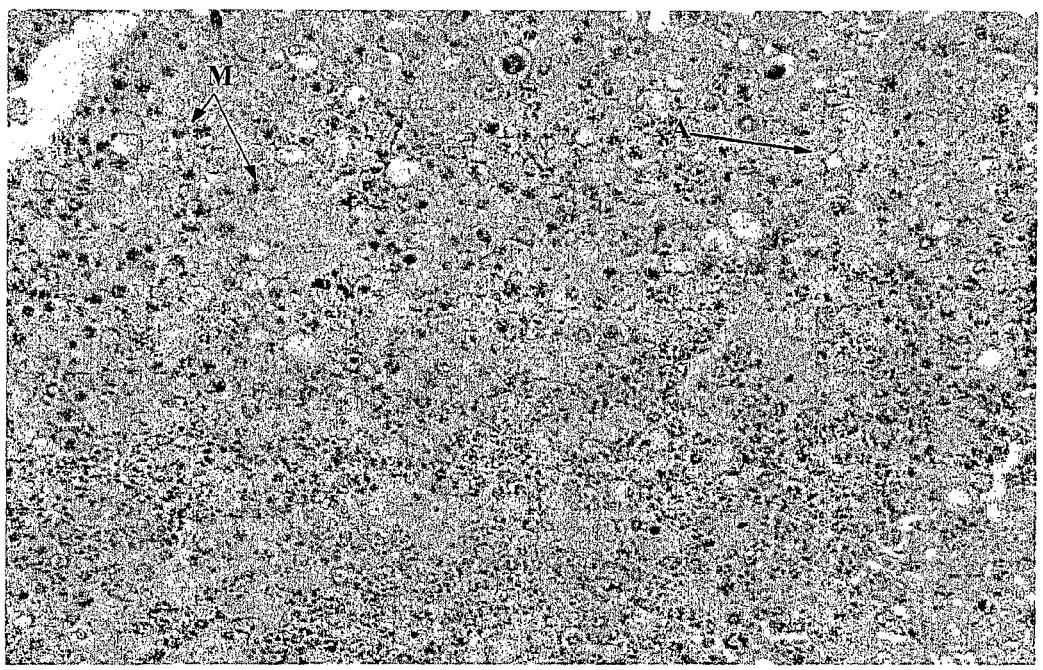
Figure 19C:
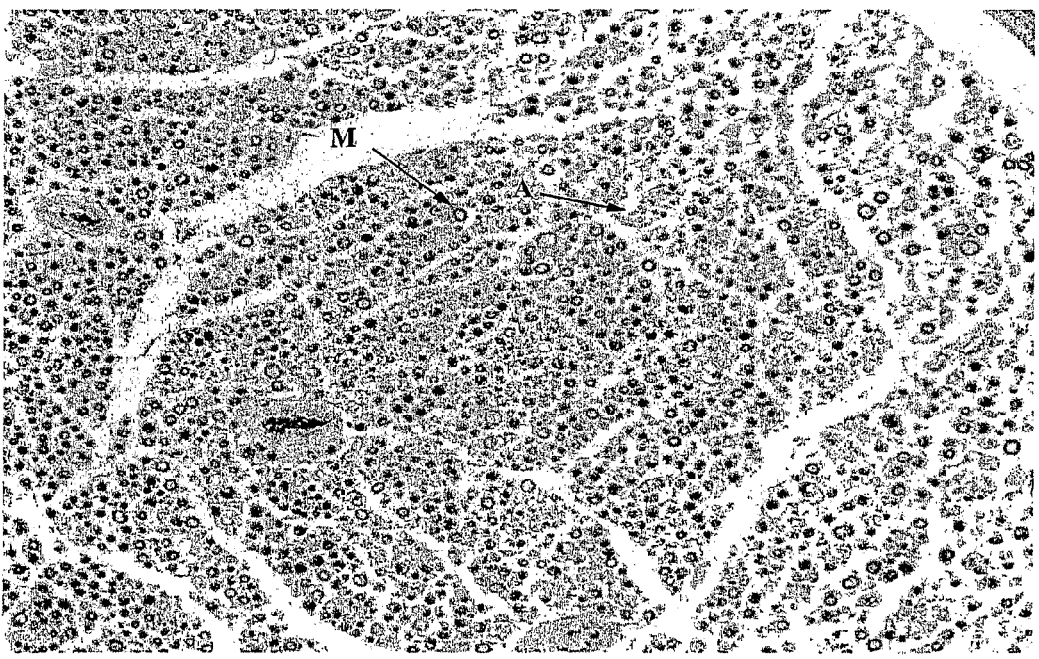
Figure 19D:
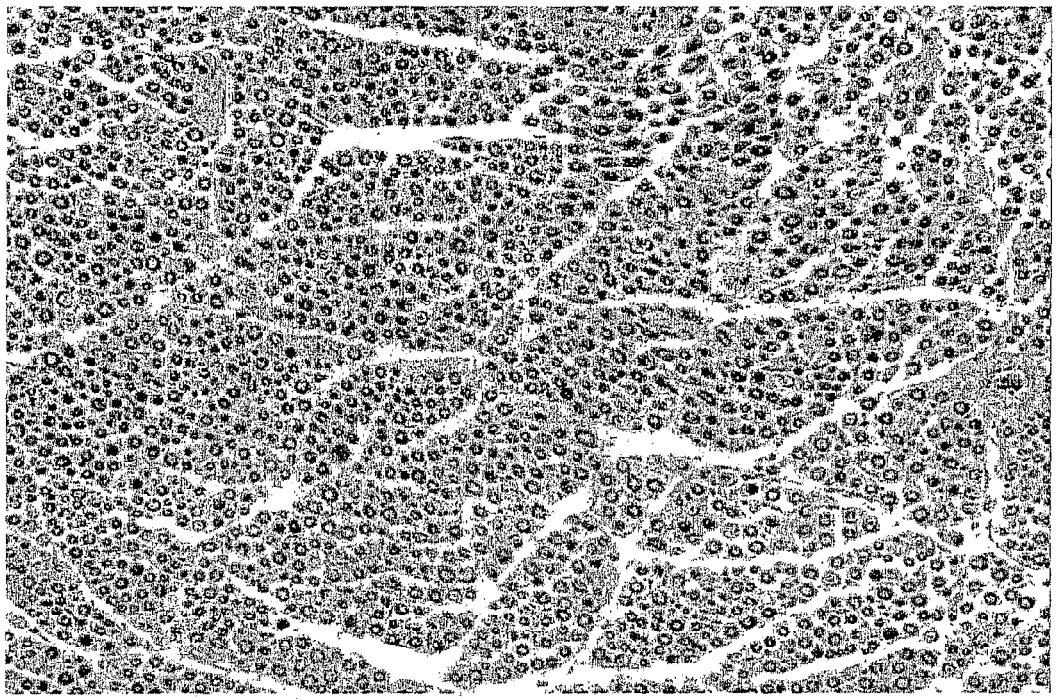
Figure 19E:
Figure 20:
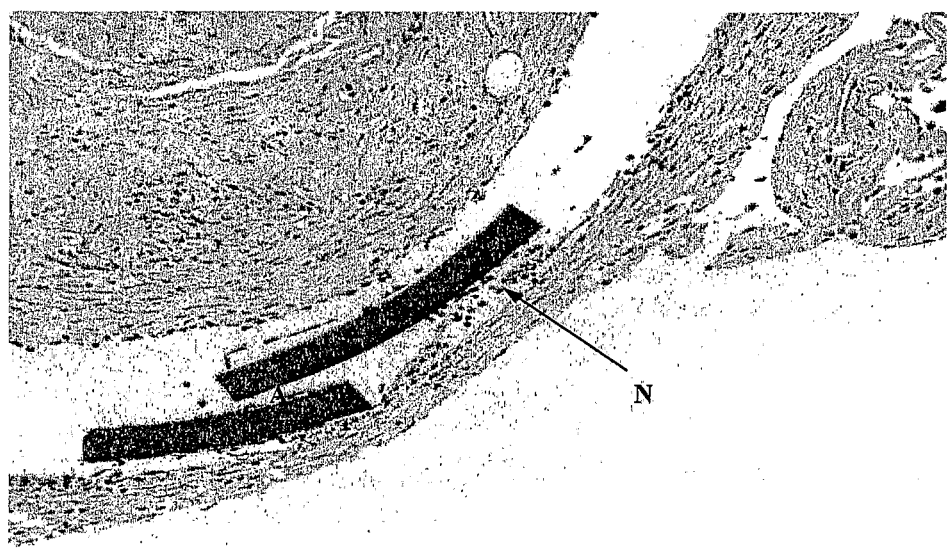
FIG. 20 is a micrograph of a cross section of the sciatic nerve and chitosan adhesive according to the present invention (A) surrounded by neutrophils (N) four days post-operatively (H&E, ×20)

The histology of the sciatic nerves showed that part of the axons underneath the irradiated adhesive was demyelinated, signalling potential thermal damage (FIG. 19a, b). The proximal and distal parts of the operated nerve, about 0.5 cm apart from the irradiated site, appeared less affected by the heat with myelinated axons retaining their normal morphology if compared to controls (FIGS. 19c-e). Neutrophils were also visible around the adhesive, suggesting that an acute inflammation response was triggered (FIG. 20). The acute shear stress of the adhesive bonded to nerves was 11.1±1.9 KPa (n=3). The chitosan collars failed at tissue interface under stress.

Discussion

The above experiments describe a novel light-activated adhesive that is insoluble in water and has improved mechanical properties compared with existing solders. The chitosan adhesive (group I) bonded to sheep intestine with a relatively high shear stress (~14.7 KPa, maximum load ~0.50 N) and also demonstrated an E modulus of ~7.3 MPa, which resulted in all the adhesive strips investigated detaching from the tissue without breaking. When compared to the conventional albumin-based solders used in earlier work by the inventors, the chitosan adhesive strips proved to withstand a higher maximum load (~0.19 N) than that of albumin strips (~0.11 N) of the same surface area (~13 mm²). It is problematic to compare the shear stress of chitosan and albumin strips because the latter ones failed either cohesively or at the tissue interface under a pulling force.

The laser-activated adhesive was also stronger than the soluble chitosan gel, which was modified with UV crosslinkers (~3.1 KPa).

Chitosan adhesive strips demonstrated an initial adhesion to tissue prior to laser irradiation (~1.9 KPa), in agreement with previous reports. Such adhesiveness was greatly enhanced by the laser as the IG dye converted photons into heat that supposedly diffused to the tissue interface, enhancing the bonding between chitosan and tissue. The mechanism responsible for this photo-adhesiveness is not yet clear, although the inventors hypothesize that the heat vaporizes the acetic acid solution, contained in the chitosan strip, at the tissue/adhesive interface. These acidic vapours along with the temperature increase may melt the chitosan and tissue collagen together allowing polyanionic-polycationic interactions or hydrogen bondings. Such bonding strength appeared to decrease if genipin was added in the adhesive composition to crosslink chitosan molecules for a few days, with or without laser activation (~9.1 KPa and 0.6 KPa respectively). Genipin strongly reacted with amino groups of the adhesive as witnessed by the high absorption peak at 608 nm. It might be possible that intermolecular and intramolecular crosslinking impaired the binding capability of collagen and chitosan. The free amino groups of chitosan, for example, might have diminished causing less polyanionic-polycationic interactions and hydrogen bonding with tissue collagen. Also, the chitosan crosslinking weakened the adhesive tensile strength and caused cohesive failure in 30% of the intestine repairs.

In vivo histology demonstrated that axons suffered demyelination under the laser-activated adhesive, four days post operatively. The thermal damage though was mostly limited under the adhesive as several axons in the proximal and distal sites were myelinated and preserved their normal morphology. The axon demyelination was likely due to the high fluence (~65 J/cm²) used to activate the adhesive, even if satisfactory bond strength (~11 KPa) was achieved in vitro by using a lower fluence (~46 J/cm²). The surgeon over irradiated the chitosan strips because the adhesive activation lacked a visual end point. A reduction of fluence is therefore needed to avoid or diminish nerve thermal damage; it also may prove beneficial to irradiate the adhesive with pulses rather than in continuous wave, as previously reported. In agreement with the above considerations, the ex vivo histology showed mild tissue coagulation of the serosa beneath the adhesive (~20 μm) but no carbonisation or vacuoles, when the laser fluence was 52 J/cm². The results of acute histology were most likely due to the low levels of fluence and irradiance (~52 J/cm² and 15 W/cm² respectively).

The laser raised the average temperature at the adhesive-tissue interface from 57 to 65° C.; such temperatures were recorded by the thermocouple and are an estimation of the real temperatures of the tissue interface during LTR. These measures were subjected to errors, mainly due to the thermocouple mass and the limited surface area of the adhesive probed by the thermocouple. The latter error was due to the small diameter of the thermocouple bed; this resulted in a significant temperature drop whenever the laser beam was not in the thermocouple proximity. The error due to the thermocouple mass was estimated to be ~2° C. from the manufacturer specifications. The above considerations indicate that <T>+standard deviation (~62° C.) should be the closest estimation of the true temperature at the tissue interface during LTR (FIG. 12). In addition, the moderate tissue shrinkage observed during LTR indicated that the tissue temperature might have ranged between 60 and 65° C. Such temperatures appear to be significantly lower than the temperatures used for LTR with albumin solders. In these cases, the albumin needs to be denatured at 65-70° C. to create a strong, insoluble bond to tissue. In contrast, chitosan adhesives are stable up to ~150° C. (FIG. 7) and do not liquefy, denature or melt below 70° C. like protein solders. One may assume that only the tissue collagen has to denature at 60-65° C. prior to bonding to chitosan and substantially increase the initial adhesiveness of chitosan films.

DSC thermograms showed that chitosan adhesives did not undergo a phase transition when the laser activated the adhesion of chitosan strips on tissue. Hence, the fluence characterizes the laser repair of chitosan adhesives better than the radiation dose (J/mg). The latter is more appropriate for albumin solders, which undergo a phase transition during denaturation and need a fixed amount of energy per mole to change the protein conformation (1.2±0.5 J/g). The fluence required to irradiate thoroughly (3 times) the chitosan adhesive was ~52 J/cm$^2$.

It is very important that tissue glues, solders and adhesives are not altered or degraded by aqueous solutions such as physiological fluids, which are often used to maintain the moisture of exposed tissues at operated sites. It was noticed during the experiments that the chitosan adhesives swelled, curled and dissolved in water, if not dried thoroughly. Particular attention was therefore necessary to dry the films until they became insoluble. Alternatively, the chitosan films used in earlier work were dried overnight and required to be immersed in a concentrated solution of NaOH to become insoluble. This treatment appeared to increase the film water content (~40%) and consequently the E modulus was drastically reduced (~0.77 MPa). The chitosan treatment with a concentrated solution of NaOH was avoided to preserve the high E modulus of chitosan films (~7.3 MPa).

In contrast to albumin solders, chitosan adhesives not only have the notable property of being insoluble but also exhibit important mechanical properties such as high E modulus and flexibility. Adhesives with ~20 μm thickness could sustain a shear stress of ~14.7 KPa without breaking, had an E modulus of ~7.3 MPa and could be curved or deformed over 160 degrees, returning to their initial shape with no sign of macroscopic damage. This flexibility of the chitosan adhesive allowed the surgeon to manipulate tissue without fear of it breaking or tearing. The adhesive did not fold or breakdown when manipulated with forceps and appeared to be well suited for tissue repair. The application of the adhesive on tissue was also facilitate by its adhesiveness prior to laser activation and hydrophilic properties (contact angle ~47'). For example, the chitosan strip adhered like a collar on the nerve stumps, align them end-to-end and allowed nerve rotation during the laser irradiation.

Unlike fibrinogen and albumin solders, which are derived from blood-based proteins, the chitosan adhesive is based on a polysaccharide and consequently there are no risks of viral infections associated to this novel adhesive. Furthermore, Chitosan is widely accepted as a non-toxic and biocompatible polysaccharide. Among other applications, chitosan is employed to develop skin grafts, tissue scaffolds and dietary products. Also of consideration in tissue repair is the remarkable antimicrobial properties of chitosan, which reduces potential infection.

According to $^{13}$C-NMR, the laser-activated adhesive appears to have the same chemical composition of chitosan shells derived from marine crustacean and therefore should retain the above mentioned properties of biocompatibility and non toxicity (FIG. 5). The results of the cytotoxicity test support this suggestion, with media extracted from the adhesive showed negligible toxicity to fibroblasts.

Chitosan adhesives may degrade in the body and also act as a delivery system at the repair site, with the potential of incorporating therapeutic drugs such as growth factors, antibiotics or genes to guide and enhance the wound healing process.

It has been shown that in vitro and in vivo degradation of chitosan films occurred less rapidly as the film deacetylation became higher. Chitin films were implanted in the back of rats and degraded ~25% in two weeks, while chitosan films (85% deacetylated) degraded 20% in 12 weeks. Furthermore, lysozyme degradation of chitosan has been reported. For example, 10% of chitosan films (85% deacetylated) degraded in 48 hours if incubated in buffered aqueous solution (pH~7) with lysozyme (4 mg/ml) at 37° C.

Chitosan adhesives are inexpensive and may be manufactured in a broad spectrum of shapes and dimensions to suit the organ or tissue characteristics where they are applied.

The invention claimed is:

1. A method for repairing a discontinuity in an area of tissue, said method comprising:
    applying one or more light activatable bioadhesive films to the tissue such that said area of tissue to be repaired is partially or fully covered by said one or more films, wherein the one or more films comprises comprising a chitosan and an energy converter comprising indocyanine green and wherein the energy converter is activated by non-UV light, wherein said composition does not comprise a protein and wherein the energy converter is not activated by UV light irradiating said one or more films with non-UV light from a light source so as to increase adhesion between the film and the tissue, compared to tissue that has not been irradiated.

2. A method of joining tissue, said method comprising:
    aligning and abutting edges of the tissue to be joined,
    applying one or more light activatable bioadhesive films so as to partially or fully cover said edges to be joined, wherein the one or more bioadhesive films comprises a chitosan and an energy converter comprising indocyanine green wherein the energy converter is activated by non-UV light, wherein said composition does not comprise a protein, and wherein the energy converter is not activated by UV light irradiating said one or more films with non-UV light from a light source so as to increase adhesion between the film and the tissue, compared to tissue that has not been irradiated.

3. The method of claim 1, wherein the degree of deacetylation of the chitosan is in the range from about 0 to about 90 weight % or mol %.

4. The method of claim 1, wherein the chitosan is covalently linked to a photoreactive group.

5. The method of claim 1, wherein the energy converter is activatable by light of wavelength ≥400 nm.

6. The method of claim 1, wherein the energy converter further comprises genipin dye.

7. The method of claim 1, wherein the composition comprises one or more additives selected from the group consisting of therapeutic agents, bacteriostats, wound healing agents, antimicrobials, preservatives, antioxidants, antifungals and antibacterials.

8. The method of claim 2, wherein the degree of deacetylation of the chitosan is in the range from about 0 to about 90 weight % or mol %.

9. The method of claim 2, wherein the chitosan is covalently linked to a photoreactive group.

10. The method of claim 2, wherein the energy converter is activatable by light of wavelength ≥400 nm.

11. The method of claim 2, wherein the energy converter further comprises genipin dye.

12. The method of claim 2, the composition comprises one or more additives selected from the group consisting of therapeutic agents, bacteriostats, wound healing agents, antimicrobials, preservatives, antioxidants, antifungals and antibacterials.

* * * * *